(12) United States Patent
Madura

(10) Patent No.: US 6,294,363 B1
(45) Date of Patent: Sep. 25, 2001

(54) RAPID METHOD OF PROTEASOME PURIFICATION USING PROTEINS HAVING SEQUENCE HOMOLOGY TO UBIQUITIN

(75) Inventor: Kiran Madura, Bridgewater, NJ (US)

(73) Assignee: University of Medicine & Dentistry of New Jersey, New Brunswick, NJ (US)

( * ) Notice: Subject to any disclaimer, the term of this patent is extended or adjusted under 35 U.S.C. 154(b) by 0 days.

(21) Appl. No.: 09/100,802

(22) Filed: Jun. 19, 1998

Related U.S. Application Data

(60) Provisional application No. 60/050,171, filed on Jun. 19, 1997.

(51) Int. Cl.[7] ............................. C12N 9/00; C12N 9/50; C12N 9/64

(52) U.S. Cl. ..................... 435/183; 435/183; 435/219; 435/226

(58) Field of Search .................................... 435/183, 219, 435/226

(56) References Cited

U.S. PATENT DOCUMENTS 5,132,213 * 7/1992 Bachmair et al. .................. 435/69.7

OTHER PUBLICATIONS

Wilek et al., The purification of biologically active compounds by affinity chromatography, Methods in Biochemical Analysis, 1976, 23:347–385.*

Udvardy, Purification and characterization of a multiprotein component of the Drosophila 26 S (1500 kD) proteolytic complex, J. Biol. Chem.j 1993, 12: 9055–9062.*

Mannen et al, Cloning and expression of human homolog HSMT3 to yeast SMT3 suppressor of MIF2 mutations in a centromere protein gene, Biochem. Biophys. Res. Commun. 1996, 222: 178–180.*

Fu et al, Multiubiquitin chain binding and protein degradation are mediated by distinct domains within the 26 S proteasome subunit Mcb 1, J. Biol. Chem. 1998, 23: 1970–1981.*

Baboshina et al, Novel Multiubiquitin chain linkages catalyzed by the conjugating enzymes E2epf and Rad6 are recognized by 26 S proteosome subunit 5, J. Biol. Chem, 1996, 271:2823–2831.*

Masutani et al, Purification and cloning of a nucleotide excission repair complex involving the xeroderma pigmentosum group C protein and a human homologue of yeast RAD23, EMBO J. 1994, 13:1831–1843.*

Deveraux et al, A 26 S protease subunit that binds ubiquitin conjugates, J. Biol. Chem. 1994, 269:7059–7061.*

Harakas, Biospicific Affinity Chromatography, Protein Puriffication Process Engineering, Harrison ed., Marcel Dekker, Inc., New York, 1994, pp. 259–316.*

Thrower et al, Recognition of the ubiquinin proteolitic sygnal, EMBO J. 2000, 19: 94–102.*

Ortolan et al, The DNA repair protein Rad23 is a negative regulator of multi–ubiquitin chain assembly, Nature Cell Biol. 2000, 2: 601–607.*

Schrauber et al, Rad23 links DNA repair to the ubiquitin/proteasome pathway, Nature, 1998, 391: 715–718.*

Tongaonkar et al, Reconstructing ubiquitination reaction with affinity purified components and 32–ubiquitin, Analyt. Biochem. 1998, 260: 135–141.*

Tongaonkar et al, Evidence for an interaction between ubiquitin–conjugating enzymes and the 26S proteosome, Mol. Cell. Biol. 2000, 20: 4691–4698.*

Madura et al, Degradation of Galpha by the N–end rule pathway, Science, 1994, 265:1454–1457.*

Watkins, J.F., P. Sung, L. Prakas, and S. Prakash. The *Saccharomyces cerevisiae* DNA Repair Gene RAD23 Encodes a Nuclear Protein Containing a Ubiquitin–Like Domain Required for Biological Function. *Mollecular and Cellular Biology.* 1993. 13:7757–7765.

Van Der Spek, P.J., C.E. Visser, F. Hanaoka, B. Smit, A. Hagemeuer, D. Bootsma, and J.H.J. Hoeumakers. Cloning Comparative Mapping, and RNA Expression of the Mouse Homologues of the *Saccharomyces cervisiae* Nucleotide Excision Repair Gene RAD23. *Genomics.* 1996. 31:20–27.

Biggins, S., I. Ivanovska, and M.D. Rose. Yeast Ubiquitin–Like Genes Are Involved in Duplication of the Microtubule Organizing Center. *The Journal of Cell Biology.* 1996. 133:1331–1346.

Manahan, R., C. Delphin, T. Guan, L. Gerace, and F. Melchior. A Small Ubiquitin–Related Polypeptide Involved in Targeting RanGAP1 to Nuclear Pore Complex Protein RanBP2. *Cell.* 1997. 88:97–107.

Garrett, K.P., T. Aso, J.N. Bradsher, S.I. Foundling, W.S. Lane, R.C. Conaway, and J.W. Conaway. Positive Regulation of Genral Transcription Factor SIII by a Tailed Ubiquitin Homolog. *Proc. Natl. Acad. Sci. USA.* 1995. 92:7172–7176.

Varshavsky, A. The Ubiquitin System. *Trends Biochem. Sci.,* 1997. 22:383–387.

Ciechanover, A. The Ubiquitin–Proteasome Proteolytic Pathway. *Cell.* 1994. 79:13–21.

Hochstrasser, M. Ubiquitin–Dependent Protein Degradation. *Annu. Rev. Genet.* 1996. 30:405–439.

Coux, O., K. Tanaka, and A.L. Goldberg. Structure and Functions of the 20S and 26S Proteasomes. *Annu. Rev. Biochem.* 1996. 65:801–847.

Hershko, A. The Ubiquitin Pathway for Protein Degradation. *Trends in Biochem. Sci.* 1996. 84:277–287.

(List continued on next page.)

Primary Examiner—Nashaat T. Nashed
Assistant Examiner—M Walicka
(74) *Attorney, Agent, or Firm*—Saul Ewing; Janet Reed, Esq.

(57) ABSTRACT

Disclosed are methods for rapidly and efficiently purifying proteasomes using fusion proteins having homology to ubiquitin using amino acid sequences adhered to a solid support.

4 Claims, 20 Drawing Sheets

OTHER PUBLICATIONS

Pickart, C.M. Targeting of Substrates to the 26S Proteasome. *FASEB*. 1997. 11:1055–1066.

Johnson, E.S., P.C.M. Ma, I.M. Ota, and A. Varshavsky. A Proteolytic Pathway That Recognizes Ubiquitin as a Degradation Signal. *The Journal of Biological Chemistry*. 1995. 270:17442–17456.

Johnson, E.S., B. Bartel, W. Seufert, and A. Varshavsky. Ubiquitin as a Degradation Signal. *The EMBO Journal*. 1992. 11:497–505.

Scheffner, M., U. Nuber, and J.M. Huibregtse. Protein Ubiquitination Involving an E1–E2–E3 Enzyme Ubiquitin Thioester Cascade. *Nature*. 1995. 373:81–83.

Glotzer, M., Murray, A.W., and Kirschner, M.W. Cyclin is Degraded by the Ubiquitin Pathway, *Nature*. 1991. 349:132–138. USA.

Van Nocker, S., Deveraux, Q., Rechsteiner, M., Viestra, R.D. . Arabidopsis MBP1 Gene Encodes a Conserved Ubiquitin Recognition Component of the 26S Proteasome. *Proc. Natl. Acad. Sci.*. 1996. 93:856–860. Biochemistry. USA.

Peters, J–M.., Harris, J.R., Kleinschmidt, J.A. Ultrastructure of the~26S Complex Containing the ~20S Cylinder Particle (Multicatalytic Proteinase/Proteasome). *European Journal of Cell Biology*. 1991. 56: 422–432. USA.

* cited by examiner

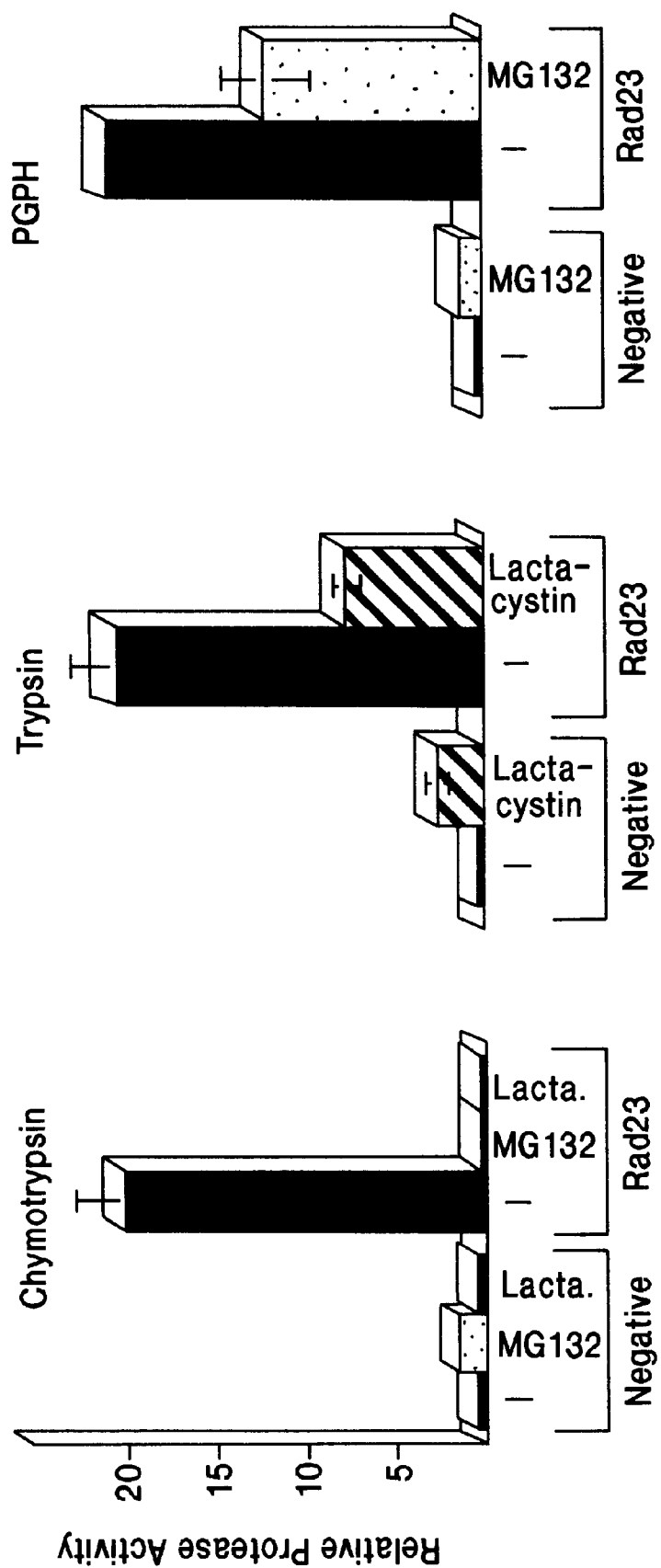

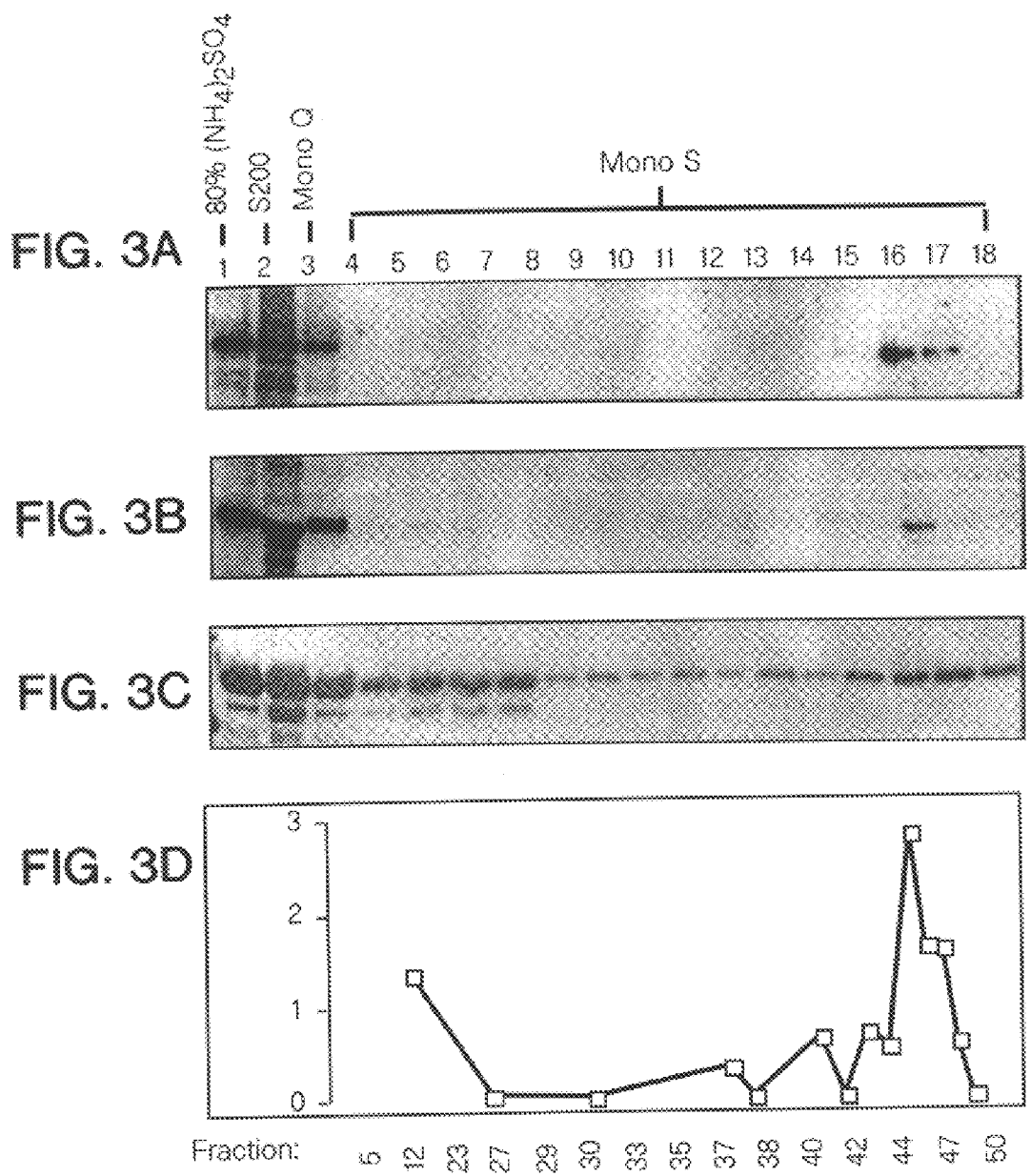

0   10   30   60 ubc4Δ
ubc5Δ ubc2Δ ubr1Δ

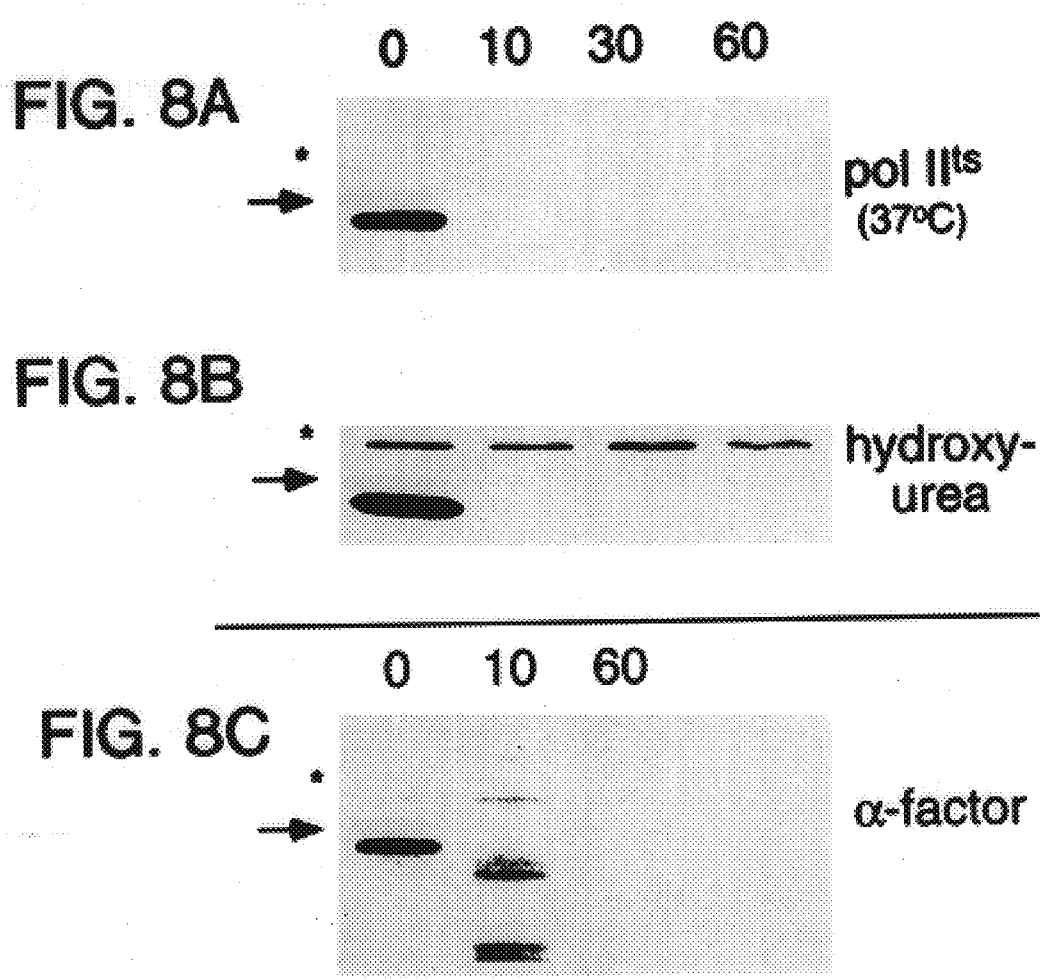

Rad23-ha         △ub Rad23-ha logarithmic growth         stationary phase wild type ufd1-1 ufd2Δ ufd4Δ ufd5Δ

FIG. 11A     0   10   30   60
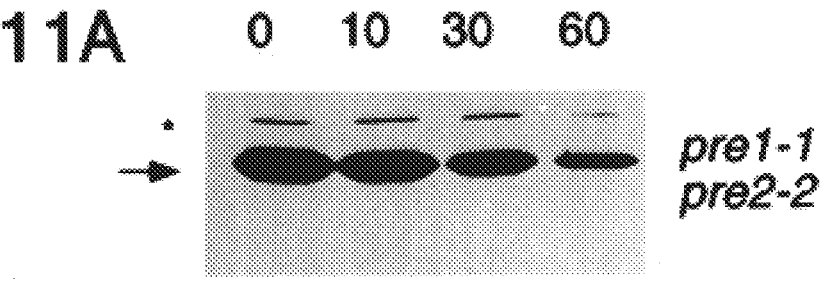
pre1-1
pre2-2
FIG. 11B
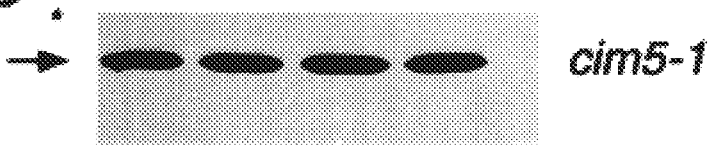
cim5-1
FIG. 11C
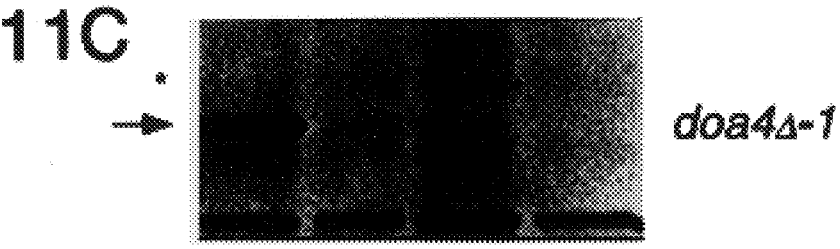
doa4Δ-1
FIG. 11D
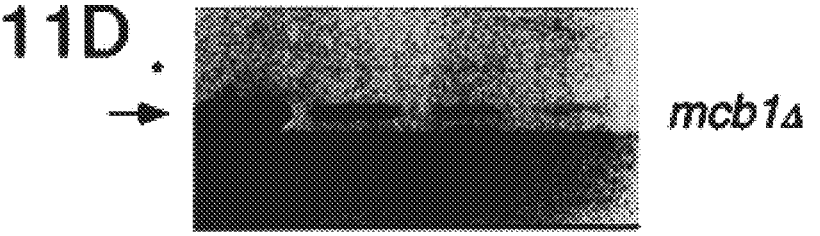
mcb1Δ
FIG. 11E
pep4Δ
prb1Δ

```
IRT1  602 VHWDDIAGLESAKYSLKEAVVYPFLRPDLFRGL..REPVRGMLLFGPPGTGKTMLARAVA
YTA6  172 VYWEDIAGLRNAKNSLKEAVVYPFLRPDLFKGL..REPVRGMLLFGPPGTGKTMIAKAVA
CIM3  206 VIYSDVGGCKDQIEKLREVVELPTLSPERFATLGIDPPKGILLYGPPGTGKTLCARAVA
CIM5  145 STYDMVGGLTKQIKEIKEVIELPVKHPELFESLGIAQPKGVILYGPPGTGKTLLARAVA

IRT1  660 TESHSTFFSISASSLTSKYLGESEKIVRALFAIAKKLSPSIIFVDEIDSIMGSRNNENE
YTA6  230 TESNSTFFSVSASSLTSKYLGESEKIVRALFYMAKKLSPSIIFIDEIDSMLTAR.SDNE
CIM3  265 NRTDATFIRVIGSELVQKYVGEGARMVRELFEMARTKKACIIFFDEIDAVGGARFDDGA
CIM5  204 HETDCKFIRVSGAELVQKYIGEGSRMVRELFVMAREFAPSIIFMDEIDSIGSTRVEGSG

IRT1  719 NESS..RRIKNEFLVQMSSLSSAAAGSNKSNTNNSDTNGDEDDTRVLVLAATNLPWSID
YTA6  288 NESS..RRIKLELLIQMSSLSSLSSATAQSEDRN......NTLDSRVLVLGATNLPWAID
CIM3  324 GGDNEVQRTMLELITQLDGF............DPRGNIKVMFATNRPNTLD
CIM5  263 GGDSEVQRTMLELLNQLDGF............ETSKNIKIIMATNRLDILD

IRT1  776 EFAARR..RFVRRQYIPLPEDQTRHVCFKKTLSHQKFTLTESDFFEIVKITEGYSGSDIT
YTA6  337 DAARR..RFSRKTVIPLPDYETRLYELKRTMAKQKNSLQDLDYELITEMTEGFSGSDLI
CIM3  363 PALLRPGRIDRKVEFSLPDLEGR.ANIFRIHSKSMSVERGIRWELISRLCPNSTGAEIR
CIM5  302 PALLRPGRIDRKIEFFPPSVAAR.AEILRIHSRKMNLTRGINLRKVAEKMNGCSGADVK

IRT1  833 SLAKDAAMGPLRDLGDKL
YTA6  394 SLAKEAAMEPIRDLGDKL
CIM3  421 SVCTEAGMFAIRARRKVA
CIM5  360 GVCTEAGMYALRERRIHV
```

FIG. 12A

RAPID METHOD OF PROTEASOME PURIFICATION USING PROTEINS HAVING SEQUENCE HOMOLOGY TO UBIQUITIN

This application claims priority under 35 U.S.C. §119(e) from U.S. Provisional Application, Ser. No. 60/050,171 filed Jun. 19, 1997, the disclosure of which is incorporated by reference herein.

Pursuant to 35 U.S.C. §202(c) it is acknowledged that the U.S. Government has certain rights in the invention described herein, which was made in part with funds from the the National Institutes of Health (GM-52058).

FIELD OF THE INVENTION

This invention relates to the field of proteolytic degradation of cellular proteins. More specifically, rapid and efficient methods for proteasome purification from various cell types are disclosed. Also provided are novel methods for use of the proteasome components so purified.

BACKGROUND OF THE INVENTION

Several publications are referenced in this application by author name and year of publication in parentheses in order to more fully describe the state of the art to which this invention pertains. Full citations for these references are found at the end of the specification. The disclosure of each of these publications is incorporated by reference herein.

The degradation of cellular proteins is necessary for the biological well-being of all organisms. Regulators of cell growth and development, and components of the immune and cellular defense mechanisms are regulated by proteolysis. Membrane receptors and transcription factors activated by cytokines, such as interleukins and interferons, are regulated by protein degradation.

The major pathway of intracellular proteolysis involves the ubiquitin/proteasome system. Ubiquitin, a 76 amino acid polypeptide, is the most highly conserved protein in eukaryotic evolution. There are only 3 amino acid differences between yeast and human ubiquitins. Extensive studies during the past decade have shown that the covalent attachment of ubiquitin to cellular proteins marks them for destruction. Substrates that are linked to ubiquitin are degraded by a multicatalytic protease called the proteasome. During the past few years many targets of the ubiquitin/proteasome system have been discovered and remarkably they include a broad range of regulators of cell growth. Some of the proteins destroyed by the ubiquitin/proteasome system include cyclins, cyclin-dependent kinases (CDK's), NFkB, IkBα, cystic fibrosis transduction receptor, p53, ornithine decarboxylase (ODC), 7-membrane spanning receptors, Cdc25 (phosphotyrosine phosphatase), Rb, Gα, c-Jun and c-Fos.

The ubiquitin/proteasome pathway is also essential for the stress-response and for the generation of antigenic peptides in MHC Class I molecules. It is clear that defects in the functioning of the ubiquitin/proteasome system can have severe consequences on biological homeostasis. Indeed, mutations that affect the degradation of many of the proteins listed above have been associated with tumorigenesis.

The 26S-proteasome comprises two distinct sub-complexes. The core complex has a sedimentation velocity of 20S and contains a variety of degradative activities. The 20S core is highly conserved across evolutionary distance and consists of a barrel of 4 rings. Each ring contains 7 subunits of either α class or α class. The rings are oriented so that two α-subunit-containing rings are on the outside, while two β-subunit containing rings are juxtaposed on the inside. Thus, the 20S core is identical at its two ends. The x-ray structure of the archaebacterial proteasome has recently been resolved and was shown to contain a narrow pore in each α ring, and a large central cavity formed by the β rings. Accordingly, the central cavity is not exposed to the cellular environment, thereby preventing non-specific degradation of cellular proteins. Proteins targeted for degradation are first threaded through the narrow pores in the a rings before they gain access to the central catalytic cavity.

The second sub-complex, referred to as the 19S-regulatory complex, binds to the ends of the 20S core and regulates access of cellular proteins to the catalytic cavity. The 19S complex, together with the 20S core make up the 26S-proteasome. The 19S complex has at least 6 distinct ATPase subunits which are thought to promote unfolding of proteolytic substrates so that they can be channeled through the narrow pores of the 20S core. The 19S complex contains as many as 20 subunits, which include a multiubiquitin-chain binding protein, isopeptidases and at least 6 ATPases. To date, many of these additional subunits remain uncharacterized.

The Rad23 gene of *S. cerevisiae* is necessary for efficient nucleotide excision repair of damaged DNA. In vitro studies indicate that this factor may play a role in assisting the assembly of the repair complex at the site of damage. Accordingly, interactions between Rad23p and other repair proteins including Rad4p, Rad14p, and subunits of TFIIH have been proposed. Thus far, however, the exact biochemical function of Rad23p in DNA repair has remained unclear.

Rad23p has an $NH_2$-terminal domain with striking homology to ubiquitin (22% identity, 43% homology). Watkins et al. have shown that this ubiquitin-like domain is required for repair activity of the protein and that the domain can be replaced by the sequence of wild-type ubiquitin. In addition, a family of proteins with similar ubiquitin-like domains have been discovered. Unfortunately, these family members have diverse species of origin and apparently disparate functions and thus have provided no clue as the exact role of this domain.

As noted above, impaired activity of the proteasome is implicated in many diseases in humans. This observation has stimulated considerable research activity in the identification of novel therapeutic agents for inhibiting and/or stimulating the activity of the proteasome. These studies have been hindered by the inefficient, time-consuming, biochemical protocols available for the purification of proteasomes. The present invention describes a rapid and efficient proteasome purification method and provides novel methods of use of various proteasome subunits so purified.

SUMMARY OF THE INVENTION

The present invention provides compositions and a rapid and efficient method for the purification of proteasome complexes from a variety of cell types. In accordance with the present invention, it has been discovered that the ubiquitin-like N-terminal domain of a yeast protein, Rad23, has high affinity for the proteasome. Accordingly, this domain or homologues thereof may be immobilized to a suitable solid support and used to isolate the proteasome from cell lysates. Following removal of non-specifically bound proteins, the proteasomes are eluted. This method will facilitate the molecular characterization of the as yet unidentified subunits of the proteasome. Ubiquitin-like domains (UbL) in cellular proteins vary slightly between species. In one embodiment of the invention, UbL-domains from a given species will be used for proteasome purification from cell lysates derived from cells of that species.

Another aspect of the invention is a kit of materials useful in performing the proteasome purification method of the invention. A kit according to this aspect of the invention comprises a solid support to which a UbL of interest has been affixed as well as suitable buffers for eluting proteasome preparations.

In a further embodiment of the invention, it has been discovered that this same N-terminal ubiquitin like domain of Rad23, UbL$^{R23}$, functions as a degradation signal in actively growing cells. Fusion proteins comprising this domain are provided herein. Reporter proteins attached to the UbL domain (UbL$^{R23}$-reporter) are rapidly degraded in logarithmically growing cells. Since a primary feature of malignant cells is the aberrant rate of cell growth, the UbL$^{R23}$-reporter provides a powerful way to assess the proliferative potential of tumor cells. In yet another embodiment of the invention, the efficacy of anti-cancer drugs can be assessed by determining the stability of the UbL$^{R23}$-reporter fusion proteins.

In a further aspect of the invention, compositions and methods are provided for enhancing the thermostability of fusion proteins containing the UbL domain. Such fusion proteins may be used to advantage in chemical reactions requiring thermostable reagents, such as the polymerase chain reaction (PCR). In this embodiment of the invention, DNA constructs are generated wherein a DNA sequence encoding a UbL-domain is operably linked to a DNA sequence encoding the protein to be thermostabilized using standard molecular biological techniques. Following expression of the DNA construct in a suitable host cell, the thermostable fusion protein is purified and utilized in biochemical assays requiring high temperatures.

In summary, the methods and kits of the invention are particularly useful for the assessing proteolytic degradation of cellular components via the proteasome. The DNA constructs of the invention encoding fusion proteins comprising UbL domains are useful for assessing the proliferative potential of malignant cells. UbL domains may also be utilized to enhance the thermostability of fusion proteins.

BRIEF DESCRIPTION OF THE DRAWINGS

FIG. 1A depicts the positions of [$^{35}$S] GST fusion proteins and [$^{35}$S] Rad-HA. Yeast strains simultaneously expressing the Rad4-HA and each of the GST-fusion proteins were metabolically labeled with $^{35}$S-methionine for 10 minutes. Extracts were prepared and adsorbed to glutathione-Sepharose. Beads were washed extensively and bound proteins resolved by SDS-PAGE and detected by fluorography. FIGS. 1A, 1B and 1C, Lane 1, GST; lane 2; GST-Rad23; lane 3 GST$^{\Delta UbL}$RAd23 and lane 4, GST-UbL$^{R23}$. Rad4-HA is detected in lanes 2 and 3 indicating that it interacts with C-terminal sequences in Rad23. Non-specific interactions of other cellular proteins with GST-UbL$^{R23}$ are indicated by asterisks. FIG. 1B is an immunoblot showing that Cim5 and Cim3 interact with GST-Rad23 and GST-UbL$^{R23}$. FIG. 1C shows that the complex that interacts with GST-Rad23 and GST-UbL$^{R23}$ contains the 20S subunit Pup1-HA. The additional band (asterisk) may represent a precursor form of Pup1-HA. FIG. 1D is a blot showing that native Rad232 can be precipitated on FLAG-agarose beads in extracts derived from a yeast strain expressing Pre1-FLAG, an epitope tagged derivative of a 20S β-subunit. FIGS. 1D and 1E, lane 1, extract from Pre1-flag cells; lane 2 extracts from negative control extract lacking Pre-1-FLAG. FIG. 1E is a blot showing that extracts containing FLAG-Rad23 can specifically precipitate Cim3 and Cim5 on FLAG-agarose beads. These subunits were not recovered from extracts containing a control vector lacking FLAG-Rad23 (lane 2).

FIG. 2 is a series of graphs depicting the proteolytic activity associated with UbL$^{R23}$. Flag-Rad23 was immunopurified and incubated with peptide substrates. A control reaction with a strain expressing an unrelated protein is also shown (Negative). The relative levels of chymotrypsin, trypsin and PGPH-like activities, and the effect of proteasome inhibitors MG132 and lactacystin are shown. A (−) symbol indicates the absence of the inhibitor. The values represent the average of three measurements.

FIG. 3 is fractionation data showing that Gst-R23, Rad4-HA and Cim5 are components of a high molecular weight complex. FIG. 3A is a Coomassie stained gel showing Mono-S fractions isolated following incubation with glutathione-sepharose. Bound proteins were separated by SDS-PAGE. FIGS. 3A, 3B, and 3C show western blots treated sequentially with antibodies against HA (FIG. 3A), Cim5 (FIG. 3B) and Rad23 (FIG. 3C). FIG. 3D is a graph showing the ATPase activity corresponding to the Mono-S fractions isolated.

FIG. 5A shows that toxicity in yeast is caused by overexpressing the N-end rule pathway (CSY13, top). This toxicity is suppressed by high levels of RAD23 (CSY41, left), or in rad23Δ (CSY41, right). Isogenic yeast strains were grown in minimal medium containing galactose and lacking appropriate nutrients to maintain plasmids. FIG. 5B is a graph showing that Rad23-ha can complement rad23Δ. Exponential-phase yeast cells (JD47-13C; RAD23, closed squares, CSY85; rad23Δ, closed circles, and CSY131; CSY85 expressing Rad23-ha, open circles) were exposed to 15, 45 and goJ/m$^2$ UV light (n=3).

FIG. 7A: Rad23-HA stability was measured in logarithmic- and stationary-phases of growth. The numbers at the top indicate minutes in chase medium. Rad23-HA (arrow) and a sepharose-interacting yeast protein (*) are indicated in this and subsequent figures. FIG. 7B: Stationary-phase yeast cells were labeled for 20 minutes and extracts were prepared to monitor the abundance of $^{35}$S-Rad23-HA. The numbers at the top refer to samples withdrawn during the labeling (in minutes), and those indicated as + refer to minutes in chase medium lacking $^{35}$S-label. Total $^{35}$S-protein was also resolved on a second gel to follow the levels of other cellular proteins (data not shown). FIG. 7C: The stability of Rad23$^{1-369}$ is shown in logarithmic-and stationary-phase cells. This C-terminal truncated allele does not possess a HA epitope but displays growth-stage specific degradation similar to Rad23-HA (FIG. 6A above) and UbL$^{R23}$-LacZ (FIG. 9B). FIG. 7D shows the degradation of other substrates of the ubiquitin system are unaffected by growth conditions. (R-β-gal is a substrate of the N-end rule pathway while ubiquitin-proline-β-gal is a substrate for the ubiquitin-fusion degradation (UFD) pathway. Met-β-gal is not a substrate of either pathway and therefore is stable in both logarithmic and stationary phase cells.

FIGS. 8A–8C are gels showing that transient growth-arrest does not affect Rad23-HA stability. The growth of exponential stage cells was arrested and Rad23-HA stability was measured. FIG. 8A: RYB 262 contains a temperature-sensitive allele of RNA polymerase II. The growth of RY262 expressing Rad23-HA was arrested at 37° C. and pulse-chase analysis was performed. FIG. 8B: Hydroxyurea was added to exponentially growing cells (JD47-13C) expressing Rad23-HA and incubated for 2 hours at 30° C. Pulse-chase analysis was carried out when approximately 75% of the cells had arrested growth. FIG. 8C: A bar1-1 strain expressing Rad23-HA was exposed to 10 ng/ml α-factor, and pulse-chase analysis was performed when approximately 95% of the cells had arrested in G$_1$.

FIG. 9A: $^{\Delta UbL}$Rad23-HA was expressed in JD47-13C and stability was compared to Rad23-HA in exponential phase. FIG. 9B: UbL$^{R23}$ was linked to β-galactosidase and the stability of UbL$^{R23}$-LacZ was determined in JD47-13C. A cluster of protein bands corresponding to UbL$^{R23}$-LacZ was detected in stationary-phase extracts and are indicated by the bracket. UbL$^{R23}$-LacZ was almost undetectable in exponential-stage cells.

FIGS. 11A–11E are a series of gels showing that Rad23-HA is degraded by the proteasome. The in vivo stability of Rad23-HA in proteasome and vacuolar mutant strains is shown. FIG. 11A, pre1-1/pre2-2; FIG. 11B, Cim5; FIG. 11C, doaΔ-1; FIG. 11D. mcb1Δ; FIG. 11E, pep4Δprb1Δ. An arrow indicates the position of Rad23-HA. A protein of approximately 70 kD which binds Sepharose non-specifically is indicated by the asterisks.

FIGS. 12A and 12B are a sequence alignment and graph showing that Rad23 interacts with a putative subunit of the 26S proteasome. Rad23p was linked to lexA and Irt1 was isolated in a 2-hybrid experiment. FIG. 12A shows the amino acid sequence corresponding to the ATPase domain of Irt1 is aligned with the sequence of closely related homologs of 26S proteasome subunits. FIG. 12B is a graph showing that the interaction between Rad23 and Irt1, and 3 C-terminal truncated alleles of Irt1, as determined by measuring β-galactosidase activity in the 2-hybrid yeast strain harboring both plasmids. The data are representative of 6 independent measurements and are indicated in Miller units.

FIG. 13A: Lane 1 contains a GST control, and lanes 2–6 contain GST linked to UbL$^{R23}$, Ub, UbL$^{DSK}$, UbL$^{HRA}$ and UbL$^{HRB}$ Yeast strains expressing the GST linked proteins as well as Pre1-Flag, FIG. 13B. The blot was developed with anti-Flag antiserum (Kodak). The position of molecular weight markers are indicated.

In FIG. 14A GST-UbL$^{HRA}$ and GST-UbL$^{HRB}$ were purifed and incubated with Hela cell S100 extract. Lane 1 contains a GST negative control, while lanes 2 and 3 contain GST-UbL$^{HRA}$ and -UbL$^{HRB}$. Lane 4 contains GST-UbL$^{R23}$ interacting proteins. Hela S100 extracts were incubated with GST, GST-UbL$^{HRA}$ and GST-UbL$^{HRB}$ and bound proteins were separated by SDS-PAGE and the western blot incubated with Cim5-specific antibodies, which crossreacts with the human counterpart Mss1. In FIG. 13B, a similar set of GST linked proteins were incubated with purified 19S/PA700 and the bound proteins separated by SDS-PAGE and visualized by staining with silver nitrate. The profile of subunits that comprise the 19S/PA700 particle is shown in lane 1. Molecular weight standards are indicated in lane 5. (Lanes 1–5 were from the same gel).

DETAILED DESCRIPTION OF THE INVENTION

Figure 1A:
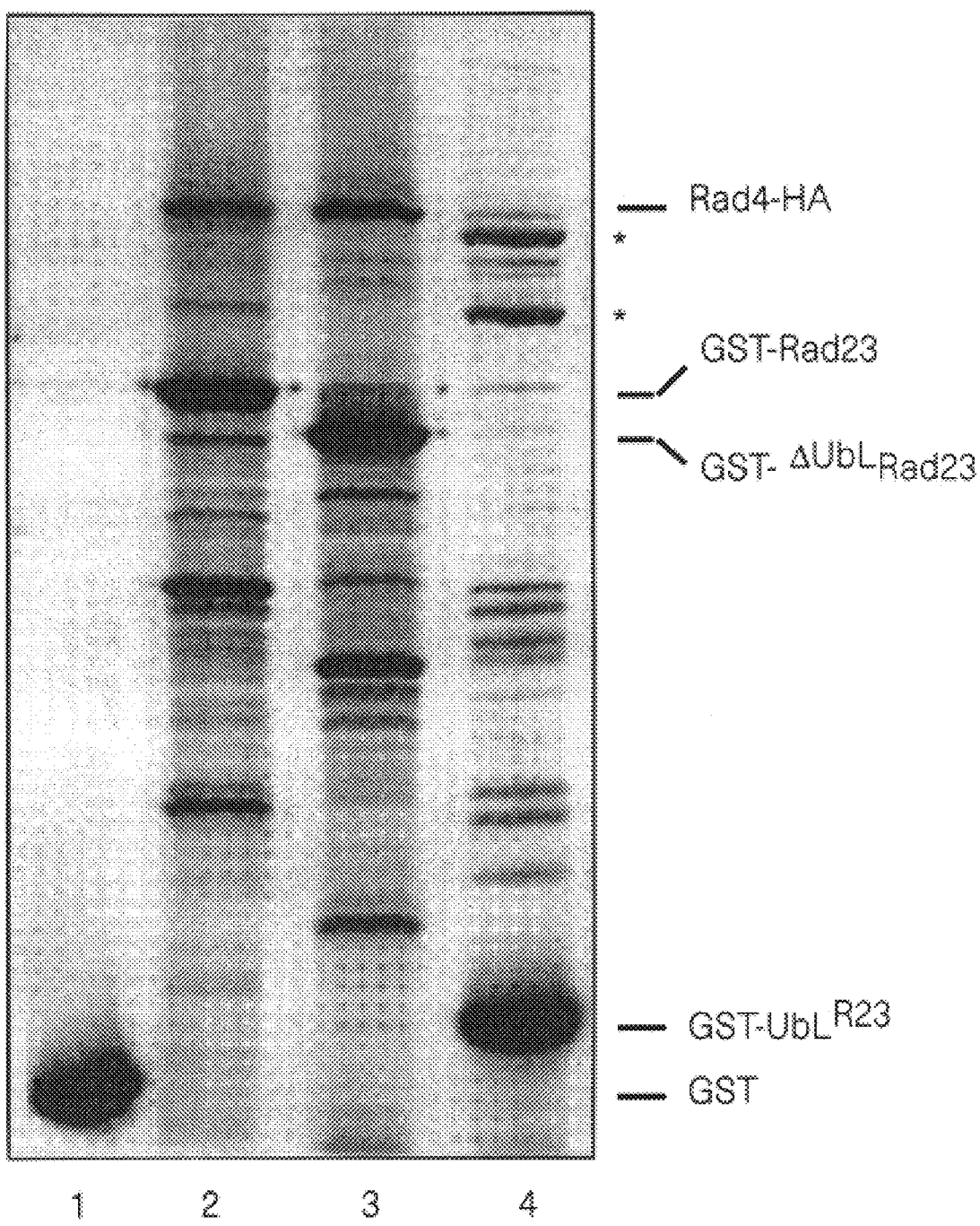
FIGS. 1A–1E are an autoradiograph and western blots of cell extracts showing that Rad4-HA interacts with Rad23 and that Rad23 interacts with the 26S proteasome. Rad4 plays a role in DNA repair and stably interacts with Rad23.

The proteasome is an essential component of the ATP-dependent proteolytic pathway in eukaryotic cells and is responsible for the degradation of most cellular proteins. The 20S (700 kDa) proteasome contains multiple peptidase activities that function through a new type of proteolytic mechanism involving a threonine active site. The 26S (2000 kDa) complex, which degrades ubiquitinated proteins, contains, in addition to the 20S proteasome, a 19S regulatory complex composed of multiple ATPases and components necessary for binding protein substrates. The proteasome has been highly conserved during eukaryotic evolution, and simpler forms are found in archaebacteria and eubacteria.

The post-translational attachment of ubiquitin (Ub) to cellular proteins is implicated in a broad range of biological activities primarily involving protein degradation (Hershko 1991). Ubiquitin is mobilized through several trans-thiolation steps which precede its isopeptide linkage to cellular substrates. Ubiquitin is activated by adenylation of its C-terminal glycine residue by the ubiquitin activating enzyme, E1 (Hershko 1991). Activated Ub is transferred from E1 to a family of ubiquitin-conjugating enzymes (E2's or Ubc's) which play significant roles in substrate selection. Emerging evidence suggests that the transfer of Ub to a cellular substrate may require an additional factor termed E3/Ub-protein ligase (Hershko 1991; Scheffner et al. 1995), or Ubr1/n-recognin (Varshavsky 1992). A well studied substrate targeting mechanism of the ubiquitin system is the N-end rule pathway (Varshavsky 1992), whose overexpression inhibits the growth of haploid yeast cells (Madura and Varshavsky, 1994). RAD23, a subunit of the nucleotide excision repair complex was isolated in a search for suppressors of this growth defect. The present invention describes the biochemical analysis of alleles of Rad23 (Rad23-HA and Rad23-FLAG). It appears from these studies that Rad23 is involved in both DNA repair and the ubiquitin protein degradation pathway.

Previous studies have demonstrated that mutations in RAD23 (rad23Δ) result in a defect in the repair of UV-irradiated DNA, which is manifested by an intermediate sensitivity to DNA damage (Friedberg et al. 1995). The moderate sensitivity of rad23 to UV light is contrasted by the severe defects observed in other excision repair mutants such as rad1, rad2 and rad4 which are unable to incise damaged DNA (Wilcox and Prakash 1981). The removal of DNA lesions is markedly reduced in rad23Δ but not abolished, suggesting that Rad23 plays an accessory role in nucleotide excision repair. In vitro studies showed that Rad23 forms a stable interaction with the excision repair protein Rad4 (Guzder et al. 1995b), although the biological significance of this association is unclear. Rad23 also interacts with other effectors, including the DNA damage-recognition protein Rad124 and the RNA PolII-specific transcription factor TFIIH (Guzder et al. 1995a). A previously unknown function for Rad23 in spindle-pole body (SPB) duplication was recently described (Biggins et al. 1996). These results indicate that Rad23 can participate in multiple regulatory pathways.

It has been discovered that the Rad23 N-terminal domain ($UbL^{R23}$) has a strong affinity for the 26S-proteasome and can be used to advantage to purify this proteolytic complex in a single step. Immobilizing this domain to a solid support, followed by exposure to cellular lysates results in the retention of the proteasome on the support. The proteasome can then be released from the support following the prior elution of all other non-specifically adsorbed proteins. A family of proteins having Ub-like domains have been observed in a variety of other species from yeast to humans (Toniolo et al. 1988; Wiborg et al., 1985). Ubiquitin-like domains in yeast Rad23 and Dsk2, as well as human HHR23A and HHR23B, are proteasome-interacting sequences. The attachment of $UbL^{R23}$ to a reporter protein also targeted it to the proteasome, demonstrating that this is an autonomous function of a UbL. The ubiquitin-like domain of Rad23 ($UbL^{R23}$) interacts with a complex that contains subunits of the 26S proteasome and displays ATPase and protease activities expected for this proteolytic system. In agreement with this finding, proteasome-specific inhibitors caused marked reduction in the proteolytic activity associated with $UbL^{R23}$. The ubiquitin-like domain of Dsk2 ($UbL^{DSK}$) binds the proteasome preferentially in actively growing cells. Overexpression of $UbL^{R23}$ inhibits the degradation of specific substrates of the ubiquitin pathway perhaps by saturating the proteasome targeting pathway. These results suggest that the physiological roles mediated by proteins containing ubiquitin-like motifs converge at the level of the proteasome, and may involve distinct proteasome subunits. The use of these ubiquitin-like homolog sequences for the purification of proteasomes from corresponding cell types, (e.g., human UbL-domains to purify human proteasomes or yeast UbL-domains to purify yeast proteasomes) is contemplated to be within the scope of the invention.

Kits are provided for purifying proteasomes from a variety of cell types. Such kits would include predetermined UbL domains fused to a solid support. The kit of the invention may also conveniently include a device for purifying biological samples, together with various solutions which may be used in performing the purification procedure, such as buffer(s), saline, diluent, controls and the like.

In accordance with another aspect of the present invention, it has been discovered that the half-life of Rad23-HA is tightly regulated, ranging from approximately 1 minute in actively growing cells to greater than 1 hour in stationary-phase. In contrast to the instability of the epitope-tagged Rad23-HA allele, it was previously reported that native Rad23 is stable (Watkins et al. 1993). Data presented herein reveal that Rad23 is degraded during the G1/S phase of the cell cycle. Specifically, data are described which indicate that the ubiquitin-like domain of Rad23 ($UbL^{R23}$) is an autonomous and regulated degradation signal. Two additional lines of evidence suggest a direct interaction with the proteolytic apparatus: 1) Rad23 interacts with Irt1, a protein that has strong similarity to ATPase subunits of the 26S proteasome, and 2) immunopurified 26S proteasome contains native Rad23. Although the fraction of Rad23 that is associated with the proteasome is not known, the findings presented herein strongly implicate a proteolytic function for Rad23.

Malignant cells display aberrant growth properties and do not respond to normal regulatory signals. Malignancy therefore arises because aberrant cells continue to grow in conditions when normal cells remain quiescent. Detection and treatment of proliferative disorders must begin with the clear identification of cells that manifest aberrant growth rates. Although malignant cells are often morphologically distinguishable from their wildtype counterparts, a quantitative measurement of the growth properties of cells is lacking.

In another embodiment of the present invention, methods are provided which employ $UbL^{R23}$-LacZ fusion protein(s) to assess cell growth rates in evolutionarily divergent organisms from yeast to humans. UbL-fusion proteins in rapidly dividing cells are degraded rapidly whereas those in quiescent cells remain stable. Proliferative rates are then determined based upon the half life of the fusion protein within the cell. Additionally, $UbL^{R23}$ can be linked to selectable markers, as well as genes that confer drug resistance. In these types of assays, cells that stabilize a fusion protein produced from a DNA construct composed of UbL$^{R23}$ coding sequence linked to a drug resistance gene would survive in the presence of the drug. It is expected that proliferating cells will actively degrade the fusion protein and succumb to the presence of the drug. In a quantitative assay such as this, dose titrations are employed to define the conditions that promote the killing of malignant cells without harming normal cells.

The ubiquitin-like domain UbL$^{R23}$ has been operably linked to the reporter protein β-galactosidase (UbL$^{R23}$-LacZ) to demonstrate the feasibility of this concept. In earlier studies performed in this laboratory, growth dependent degradation of native Rad23 was observed. These data suggested that UbL$^{R23}$ was an important component of the degradation signal. As proposed, UbL$^{R23}$-LacZ fusion proteins proved to be exceedingly unstable in actively growing cells but entirely stable in quiescent cells, mimicking the degradation profile of Rad23 protein.

To further assess the suitablity of using UbL$^{R23}$-LacZ fusion proteins to assess growth potential, this fusion protein was produced in cells expressing various Ras mutants. Ras proteins are highly conserved small GTP-binding regulators that control growth, differentiation and a variety of other cellular functions. Oncogenic alleles of Ras are hyperactive and do not arrest growth properly, while null mutants of Ras arrest growth prematurely. The data revealed that the level of UbL$^{R23}$-LacZ was almost undetectable in a strain expressing the oncogenic Ras mutant, while elevated levels of UbL$^{R23}$-LacZ were detected in cells lacking Ras. These findings corroborate the proposal that UbL$^{R23}$-LacZ is a suitable reporter protein to assess the proliferative potential of cells.

The strategy described above enables the identification of genetic mutants that promote or attenuate the degradation of the UbL$^{R23}$-linked chimeras. It is anticipated that such mutants would either promote or inhibit proliferation. This method also provides a way to screen for compounds that promote quiescence. For instance, if UbL$^{R23}$ is linked to a gene that confers drug resistance, the expression of drug resistance should be confined to quiescent cells, or cells whose growth has been artificially arrested.

In yet another aspect of the present invention, it has been discovered that the UbL$^{R23}$ domain confers thermostability on Rad23 and on fusion proteins to which this domain has been operably-linked. Thus the UbL domain is a cis-acting temperature stabilizer. This domain can be used to advantage to create fusion proteins with enhanced thermostability.

PCR assays utilize the Taq polymerase enzyme which functions at the higher temperatures required for PCR yet also generates errors in the amplified sequences as the enzyme exhibits reduced fidelity in DNA copying. In one embodiment of the invention, the UbL domain may be fused to a polymerase enzyme which has a reduced error rate. Such fusion proteins can be used in PCR assays to increase the fidelity of DNA amplification.

The definitions set forth below are provided to facilitate understanding of the subject matter of the present invention:

The term proteasome refers to a 26S multicatalytic protease.

The phrase N-end rule pathway relates the in vivo half-life of a protein to the identity of its amino-terminal residue. overexpression of targeting components of the N-end rule pathway in *S. cerevisiae* inhibits the growth of yeast cells.

The term promoter region refers to the 5' regulatory regions of a gene. In the present invention, the use of both strong constitutive gene promoters and inducible gene promoters is contemplated.

The term operably linked means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector. The term may also be used to describe the fusion of a nucleic acid sequence encoding a UbL domain of the invention to a second nucleic acid sequence encoding a protein of interest. Expression of the fused nucleic acid sequences results in the production of a fusion protein.

The term fusion protein refers to a chimeric protein molecule comprising two or more domains from different sources.

The term DNA construct refers to genetic sequence used to transform cells. These constructs may be administered to cells in a viral or plasmid vector.

The term reporter gene refers to a gene whose expression may be assayed; such genes include, without limitation, lacZ, amino acid biosynthetic genes, e.g., the yeast LEU2, HIS3, LYS2, or URA3 genes, nucleic acid biosynthetic genes, the mammalian chloramphenicol transacetylase (CAT) gene, the green fluorescent protein (GFP) or any surface antigen gene for which specific antibodies are available.

The term selectable marker gene refers to a gene product that when expressed confers a selectable phenotype such as antibiotic resistance on a transformed cell.

Methods of delivery of the DNA constructs of the invention to target cells include electroporation, CaPO$_4$ precipitation, lipid-based systems and microinjection. Standard methods for delivery of DNA and protocols for preparing the transforming DNA may be found in *Current Protocols in Molecular Biology*, eds. Frederick M. Ausubel et al., John Wiley & Sons, 1995.

The following specific examples are provided to illustrate various embodiments of the invention. They are not intended to limit the scope of the invention in any way.

EXAMPLE I

Rapid and Efficient Purification of Proteasomes Using RAD23 and Components Thereof Rad23 has an unusual N-terminal domain that bears a striking resemblance to ubiquitin (Watkins et al., 1993). This domain, which has been designated UbL$^{R23}$, is important for DNA repair because its elimination causes sensitivity to UV light (Watkins et al., 1993). A role for Rad23 in the ubiquitin system was suggested by its suppression of N-end rule induced toxicity, which raised the possibility of a proteolytic function in DNA repair.

Rad23 and Rad4, a well as the human counterparts HHR23-B and XPC, form stable interactions. We therefore tested whether GST-Rad23 interacts with components of the DNA repair and proteolytic pathways. We linked Rad4 to the HA epitope (SEQ ID NO: 17: Try-Pro-Try-Asp-VAl-Pro-Asp-Tyr-Ala (Rad4-HA) and found that it complemented rad4Δ. GST-Rad23 and RAd4-HA were expressed simultaneously in yeast cells and metabolically labeled with [$^{35}$S]-methionine. Radiolabeled extracts were applied to glutathione-Sepharose and bound proteins analyzed by SDS-PAGE and fluorography. Rad4-HA interacts with GST-R23. See FIG. 1A, lane 2. The interaction of Rad4-HA with GST-Rad23 did not require UbL$^{R23}$, (FIG. 1A, lane 3) demonstrating that distinct regions of Rad23 interact with the proteolytic and DNA repair pathways. Identical samples were transferred to nitrocellulose and analysed by incubation with anti-HA antibodies and, consistent with these findings, RAd4-HA was detected only in lanes 2 and 3. These findings are in agreement with a recent report showing that 21 C-terminal residues in Rad23 are important for interaction with Rad4.

Figure 1B:
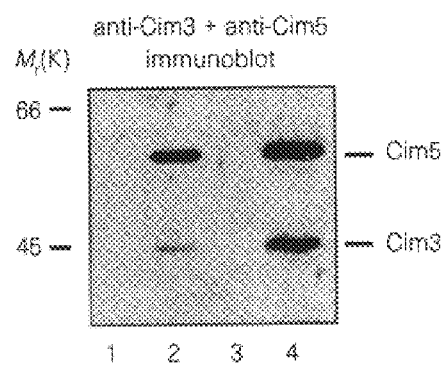
Figure 1C:
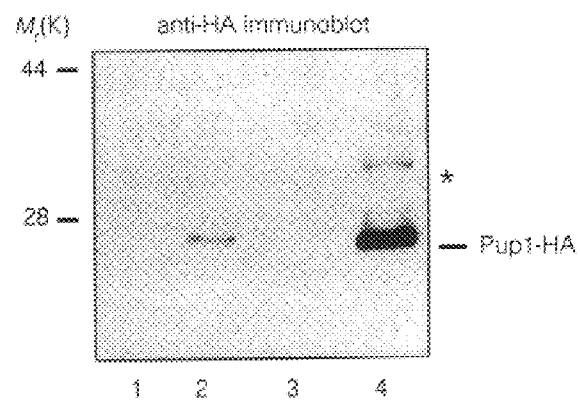
Figure 1D:
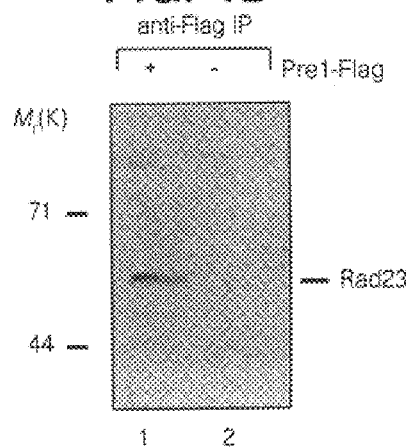
Figure 1E:
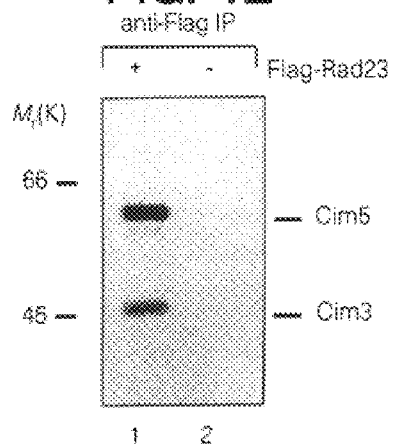

To further explore the proteolytic function of Rad23 in DNA repair, Rad23 and two truncated mutants were operably linked to glutathione-S-transferase (GST-Rad23, GST-$^{\Delta UbL}$Rad23, and GST-UbL$^{R23}$), and immobilized on glutathione-Sepharose. Western blots containing the proteins released from GST and GST-Rad23 beads were incubated with antibodies against Cim3 (Sug1) and Cim5. Cim3 and Cim5 are ATPases of the regulatory (19S) subunit of the 26S proteasome. Both Cim3 ($M_r$ 43K) and Cim5 ($M_r$ 54K) were detected in the GST-Rad23 beads (FIG. 1B, lane 2) but not in the control GST beads (FIG. 1B, lane 1). GST-UbL$^{R23}$ alone could efficiently bind a complex containing Cim3 and Cim5 (FIG. 1B, lane 4) but, a mutant lacking UbL$^{R23}$ (GST$^{\Delta UbL}$Rad23) could not (FIG. 1B, lane 3). Two variants of Rad23, bearing small epitopes on either the N-terminus (FLAG-Rad23, FIG. 1E) or the C-terminus terminus (Rad23-HA, data not shown) also interacted with the proteasome. Both Cim3 and Cim5 were detected in anti-FLAG immunoprecipitates prepared from yeast cells expressing FLAG-Rad23 (FIG. 1E). Because yeast cells expressing $^{UbL}$Rad23 fail to complement rad23Δ these findings suggest that Rad23-proteasome interaction is important for DNA repair. These data also show that UbL$^{R23}$ represents a new proteasome interaction signal. A large family of proteins bearing ubiquitin-like extensions have been identified, and our results suggest that they too have proteolytic functions.

To determine whether the GST-Rad23 interacting complex included 20S catalytic subunits, extracts from cells expressing Pre1-FLAG (28K) or Pup1-HA (33K), both of which are epitope-tagged derivatives of 20S β-subunits were analyzed. Both Pup1-HA (FIG. 1C, lane 2) and Pre1-Flag (data not shown) were detected in GST-Rad23 beads after incubation with FLAG or HA antibodies, confirming the presence of 20S catalytic subunits. GST-UbL$^{R23}$ accumulated to higher levels than than GST-Rad23, and the recovery of Pup1-HA was proportionately higher (FIG. 1C, compare lanes 2 and 4). To confirm that the findings applied to native Rad23, Pre1-FLAG was immunoprecipitated on FLAG-agarose beads and interacting proteins were resolved on SDS-PAGE. Proteins were transferred to nitrocellulose and the blots were incubated with Rad23-specific antibodies. Native Rad23 was readily detectable in immunoprecipitates containing Pre1-FLAG but not from a control extract lacking this epitope-tagged proteasome subunit (FIG. 1D). Approximately 5% of cellular Rad23 precipitated with Pre1-FLAG. This estimate is based on the amount of Rad23 that remained on the FLAG-agarose beads after 18 hours at 4° C. The in vivo interaction could be higher if the interaction with the proteasome is transient or regulated.

To examine if the Rad23 interacting complex had proteasome-specific activities we measured ATPase (Merrick, W. C., 1979), and protease activities (Heinemeyer et al., 1991). We found that high levels of ATPase activity were associated with FLAG-Rad23 (Kibel et al., 1995). Consistent with this finding, high proteolytic activity was detected against three different peptide substrates in FLAG-Rad23 immunoprecipitates. This activity was significantly reduced by the proteasome inhibitors MG132 and lactacystin (Coux et al., 1996). See FIG. 2.

To characterize the interaction of Rad4 with Rad23, extracts were prepared from cells expressing both GST-Rad23 and Rad4-HA and proteins separated on Sephacryl S-200. GST-Rad23 was detected in the void volume coincident with dextran blue, and also in fractions corresponding to its predicted monomeric size (approximately 80K). GST-Rad23, Cim5 and Rad4-HA could each detected in the high molecular weight fraction, suggesting that they are components of a single complex. See FIGS. 3A–C, lane 2.

To investigate this further, proteins in the Sephacryl S-200 void volume were chromatographed on Mono-Q. GST-Rad23, Rad4-HA, and Cim5 were detected in samples eluting at approximately 0.35 M KCl. Significantly, these fractions were previously shown to contain catalytically active proteasome (Rubin et al., 1996). Fractions that eluted between 325 and 375 mM KCl from the Mono-Q column were pooled and chromatographed on Mono-S. Cim5 and Rad4-HA again co-fractionated with with GST-Rad23 (FIG. 3A–3C, lanes 15–18) and a peak of ATPase activity copurified with the GST-Rad23 interacting complex. See FIG. 3D.

Figure 4:
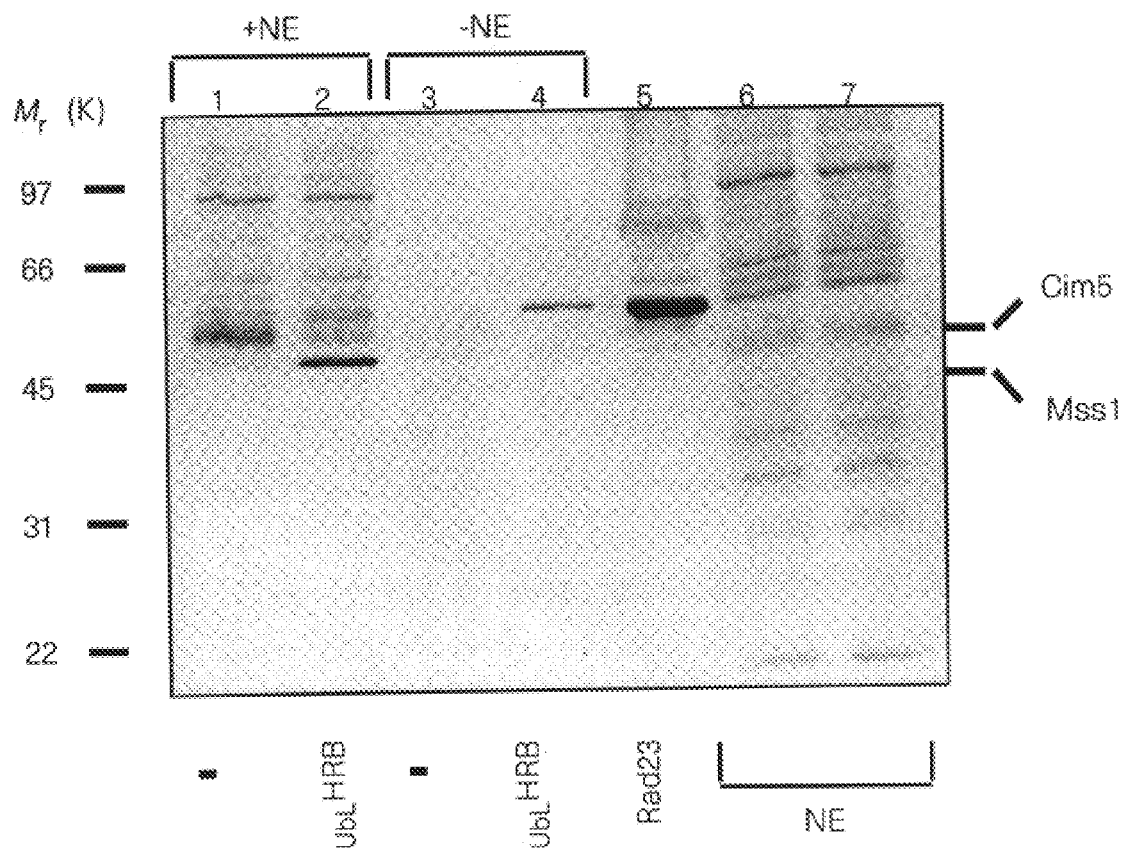
FIG. 4 is a blot showing that human HHR23-B interacts with Mss1. The ubiquitin-like domain of HHR23-B was linked to Gst (Gst-Ub$^{HRB}$) and incubated with Hela cell nuclear extracts. Mss1 was detected with Cim5 antibodies (lane 2). Cim5 interaction with Gst-R23 is also shown (lane 3).

As mentioned previously, two human homologues of Rad23, HHR23-A and HHR23-B contain N-terminal ubiquitin-like domains, suggesting that they act in a similar way to the yeast protein, Rad23. Significantly HHR23-B forms a stable interaction with XPC, the human counterpart of Rad4. To explore the functional relatedness among this class of proteins, the ubiquitin-like domain of HHR23-B (UbL$^{HRB}$) was linked to GST. GST-UbL$^{HRB}$ was immobilized on glutathione sepharose and reacted with nuclear extracts prepared from Hela cells (a gift from D. Reinberg, RWJMS, New Jersey). Cim5 antibodies revealed an interaction between Gst-UbL$^{HRB}$ and Mss1, the human equivalent of Cim5. See FIG. 4, lane 2. GST-Rad23 interaction with Cim5 (lane 4) confirmed the specificity of the antibody reaction. The evolutionary conservation of yeast and human DNA repair and ubiquitin pathways strongly suggests that the molecular interactions reported here are evidence of a novel mechanism for regulating DNA repair in yeast and humans. These findings also indicate that ubiquitin-like sequences represent a novel class of proteasome-interacting domains, and their characterization may facilitate the molecular elucidation of the mechanistic action of proteins that bear this domain.

As exemplified herein, UbL-like domains can be used to efficiently purify the proteasome. This rapid purification method enables purification from a variety of cell types. The UbL-domains may be immobilized to a solid support such as an immunoaffinity column. Following immobilization, the column is exposed to cell lysates, non-specific proteins are eluted and the immobilized proteasome subsequently purified.

Exemplary UbL-domain containing sequences for use in the methods of the present invention are set forth below:

```
UB    MQ  IFVKTLTGKTITLEVEPSDTIENVKAKIQDKEGI PP
DSK   MSLNIHIKSGQDKWEVN VAPESTVLQFKEAINKANGI PV
RAD   MVSLTF KNFKKEKVPLDLE PSNTILETKTKLAQSISCEE
HRB   MQV  TLKTLQQQTFKIDIDPEETVKALKEKIESEKGK DA
HRA   MAVTITLKTLQQQTFKIRMEPDETVKVLKEKIEAEKGR DA
212   AVHLTLKKIQAPKFSIEHDPSPSDTILQIKQHL  IS EEKA
RUB1  MI  VKVKTLTGKEISVELKESDLVYHIKE    LL   EEKE
173   EEIAAF RIFRKKSTSNLKSSHTTSNLVKKTMFKRDLLKQD
UB    D   QQRLIFAGKQLEDGRTLSDYNIQKEST LHLVLRLRGG
DSK   AN     QRLIYSGKILKDDQTVESYHIQDGHS VHLVKSQPKP
RAD   S   QIKLIYSGKVLQDSKTVSECGLKDGDQVVFMV SQKKS
HRB   FPVAG QKLIYAGKILNDDTALKEYKIDEKNFVVVMVTKPKA
HRA   FPVAG QKLIYAGKILSDDVPIRDYRIDEKNFVVVMVTKTKA
212   SHIS EIKLLLKGKVLHDNLFLSDLKVTPANSTITVMIKPNPTIS
RUB1  GIPPSQQRLIFQGKHSDDKLTVTDAHLVEGMQLKLVLTLRGG
173   PKRKLQLQQRFASPTDRLVSPCSLKLNEEKVKMFGKKKKVNPM
```

Sequences listed above:
SEQ ID NO: 1 Ub:    ubiquitin
SEQ ID NO: 2 DSK:   yeast Dsk2
SEQ ID NO: 3 RAD:   yeast Rad23
SEQ ID NO: 4 HRB:   human Rad23-B (HHR23-B)
SEQ ID NO: 5 HRA:   human Rad23-A (HHR23-A)
SEQ ID NO: 6 212:   yeast protein of unknown function that contains an internal UbL
SEQ ID NO: 7 RUB1:  yeast ubiquitin-like protein that is post-translationally conjugated to other proteins
SEQ ID NO: 8 173:   yeast protein of unknown function that contains an internal UbL Additional ubiquitin-like domain sequences for use in the methods of the present invention are set forth below:

```
SEQ ID NO: 9 SUMO1
MSDQEAKPSTEDLGDKKEGEYIKLKVIGQDSSEIHFKVKMTTHLKKLKESYCQRQGVPMNSLRFLFE
GQRIADNHTPKELGMEEEDVIEVYQEQTGGHSTV

SEQ ID NO: 10 SMT3B
MADEKPKEGVKTENNDHINLKVAGQDGSVVQFKIKRHTPLSKLMKAYCERQGLSMRQIRFRFDGQPI
NETDTPAQLEMEDEDTIDVFQQQTGGVY

SEQ ID NO: 11 SMT3A
MSEEKPKEGVKTENDHINLKVAGQDGSVVQFKIKRHTSLSKLMKAYCERQGLSMRQIRFRFDGQPIN
ETDTPAQLRMEDEDTIDVFQQQTGGVPE

SEQ ID NO:12 SMT3 yeast
MSDSEVNQEAKPEVKPEVKPETHINLKVSDGSSEIFFKIKKTTPLRRLMEAFAKRQGKEMDSLRFLY
DGIRIQADQTPEDLDMEDNDIIEAHREQIGGAT
```

SMT3:    yeast ubiquitin-like protein that is post-translationally conjugated to other proteins like ubiquitin and RUB1.

SUMO:    mammalian homolog of the yeast SMT3

Elongin: mammalian protein containing UbL that is not conjugated to other proteins parkin:  UbL-containing protein implicated in juvenile Parkinson's disease

EXAMPLE II

RAD23 and Its Role in Protein Degradation

Nucleotide excision repair is enhanced by Rad23, a member of a class of proteins that bear unusual ubiquitin-like extensions at their N-termini. Specific modifications of Rad23 cause rapid degradation via the ubiquitin/proteasome system. Surprisingly, the short in vivo half-life of these variants does not affect the DNA damage response and can be reconciled with a growth-stage specific function for Rad23. The degradation signal in Rad23 resides in its N-terminal ubiquitin-like domain (UbL$^{R23}$), which confers instability when placed on a heterologous protein. Evidence for a proteolytic function for Rad23 is suggested by its interaction with Irt1p, a protein that bears a striking resemblance to members of the ATPase subunits of the 26S proteasome. Rad23 can be co-precipitated with immunopurified 26S proteasome, implicating a proteolytic function during DNA repair.

Materials and Methods for Example II

Isolation of High-Copy Suppressors of N-end Rule Overexpression

Yeast strain KMY950 was generated by transforming JD47-13C with a 2μm-based plasmid expressing UBR1 and UBC2 from the galactose-inducible GAL1/10 promoter. The growth of KMY950 is severely impaired on galactose-containing medium due to overexpression of the N-end rule pathway (Madura and Varshavsky 1994). KMY950 was transformed (Gietz et al. 1992) with a plasmid library expressing yeast cDNAs from the GAL1 promoter (Liu et al. 1992). Based on control plating experiments, we estimated that a total of approximately $10^5$ transformants were analyzed. Plasmid DNAs that enabled KMY950 to grow on galactose-containing medium were identified and subjected to sequence analysis by the dideoxy chain-terminating method. One strong suppressor (plasmid pCEP10) encoded the complete open reading frame of the yeast RAD23 gene.

Strains, media, growth conditions and genetic techniques

S. cerevisiae strains include JD47-13C (MATa his3-Δ200 leu2-2, 112 ura3-52 trp1-Δ63 lys2-801); CSY85 (rad23Δ::URA3 in JD47-13C); CSY228 (5-FOA cured ura$^-$ derivative of CSY85); BR4 (MATα pre1-1 pre2-2 ura3-Δ5 leu2-2, 112 his3-11, 15); RY262 (MATα his4-518 ura3-52 rpb1-1); BJ5457 (MATα ura3-52 trp1 lys2-801 leu2-Δ1 his3-Δ200 pep4::HIS3 prb1Δ1.6R can1); Y791 (MATa his3-Δ200 leu2-Δ1 ura3-2 cim5-1); KMY334 (MATa his7 cdc7-4 ura3 bar1-1); CTY10-5d (MATa ade2 gal4 gal80 his3-Δ200 leu2-3, 112 trp1-Δ901 URA3-lexop GAL1-LacZ). The ubc4Δ, ubc5Δ, ubc4Δubc5Δ and the congenic wildtype strains have been described previously (Chen et al. 1993). A rad4Δ::URA3 deletion was made in MKP°; (MATαade2 lys2 can1-100 his3-Δ200 ura3-52 trp1-Δ901 leu2-2, 112). E. coli strain MC1066, bearing the pyrF74:pn5 mutation was used to select plasmids expressing yeast URA3. Yeast growth media were prepared as described previously (Guthrie and Fink, 1991). The expression of genes linked to the CUP1 promoter was induced by the addition of 0.1 mM CUSO$_4$. For pulse-chase analysis exponential-phase cells were grown to a density at A$_{600}$ of approximately 0.5 and stationary phase cultures were grown to A$_{600}$ >2.5. In experiments where we measured the stability of Rad23-ha in both conditions, stationary-phase cultures were collected (25 ml) by centrifugation, washed and resuspended in a small volume of sterile dH$_2$O. The cell suspension was inoculated into the used stationary-phase medium and fresh YPD medium, and incubated with vigorous aeration at 30° C. for 4–5 hours to enable the YPD cultures to resume exponential growth. After 4 hours at 30° C. the density of the YPD culture increased by approximately 2-fold, indicating recovery from stationary phase.

Plasmids, DNA Manipulations and DNA Sequencing

Recombinant methods were performed by standard procedures (Ausubel, 1992). We amplified RAD23 by polymerase chain reaction (PCR) using oligonucleotide primers (#42: 5'-GCGAATTCATGGTTAGCTTAACC-3' (SEQ ID NO: 13) and #41: 5'-GCGGTACCCGTCGGCATGATCGCTG-3') (SEQ ID NO: 14). The primers introduced an EcoRI site on the 5' end and a KpnI site on the 3' end of the DNA fragment. A 1.2 kb EcoRI-KpnI PCR DNA fragment was ligated to EcoRI/KpnI-digested pKM1362-2 (Madura and Varshavsky, 1994), yielding plasmid pCS8. In pCS8, Rad23p is linked to a C-terminal HA-epitope (Rad23-ha) and is expressed from the CUP1 promoter. To construct rad23Δ a 4.8 kb EcoRI fragment containing a disrupted allele of RAD23 was excised from pDG28 (Madura and Prakash, 1990) and used to replace the wild-type gene in JD47-13C by homologous recombination (Rothstein 1991). The resulting rad23Δ::URA3 strain (CSY85) was plated on 5-FOA containing medium to isolate CSY228, a ura-derovatove (Boeke et al. 1984). To make Rad23-ha lacking its N-terminal ubiquitin-like domain (pWP1), DNA sequence encoding codons 78 to 398 were amplified using oligonucleotide primers (88: 5' GCGAATTCATGACGAAGACCAAACTAACAGAA-3'; SEQ ID NO:15, and 41: SEQ ID NO: 14) and ligated to pKM1362-2, as described above. Similarly, DNA sequence corresponding to codons 1-77 (UbL R$^{23}$) were amplified and ligated to LacZ in pKM1362-2 to yield UbL$^{R23}$-LacZ. Oligonucleotide primers, specific to the coding sequence of β-galactosidase gene (beginning at codon # 8), were used to amplify LacZ.

Two-hybrid System Screen and Cloning of IRT1

RAD23 was isolated on a Dra1-EcoR1 DNA fragment, treated with DNA Pol1-Klenow, and ligated to similarly treated BamH1 digested pBTM116 (Paetkau et al. 1994). The resulting plasmid DNA, encoding lexA-Rad23, was transformed into CTY10-5d. Yeast genomic DNA libraries were transformed into CTY10-5d expressing lexA-Rad23p and approximately 2.4×10$^5$ transformants were screened to identify blue colonies on indicator plates. Plasmid DNAs were purified from colonies that displayed an interaction (based on the color assay), and were subject to DNA sequence analysis using the primer 5'-GAAGATACCCCACCAAAC-3', SEQ ID NO: 16, and then compared to sequences in GenBank using the BLAST algorithm. The DNA sequence in plasmid pDG869 corresponded to an open-reading-frame designated YER047C on Chromosome V. A Lambda clone encompassing this region (#6379) was obtained from the American Type Culture Collection, and a 3.2 kb Pst1 DNA fragment was isolated and ligated to Pst1 digested pUC19 (pRK1). A 3.5 kb BssS1 DNA fragment was purified from pRK1, treated with DNA Pol1-Klenow, and ligated to the Sma1 site in pUC8 (pRK16). A 3.2 kb EcoR1 DNA fragment was isolated from pRK16 and ligated to EcoR1 treated pGAD424, to generate an in-frame fusion of Irt1p to the activation domain of Gal4 (pRK26). To generate C-terminal truncations of Irt11p plasmid pRK26 was treated with Bsu361, Bcl1 and Nde1 and religated to yield alleles encoding residues 1-567, 1-243 and 1-172, respectively. Measurement of β-galactosidase activity were as described in Paetkau et al., 1994.

Pulse-chase and immunoprecipitation

Pulse-chase analysis, protein extraction, quantitation and immunoprecipitation of HA-tagged and β-gal fusion proteins were carried out as described previously (Madura and Varshavsky, 1994). Yeast cells were labeled for 5 minutes with $^{35}$S-Translabel (ICN Pharmaceuticals), and the reaction was terminated by the addition of buffer containing cycloheximide and excess cold methionine and cysteine. Immunoprecipitations were carried out using equal cpm of lysate (that were adjusted to equal volume). Immune complexes were captured on Protein-A Sepharose and resolved on SDS-polyacrylamide gels. Autoradiographic images were quantitated by PhosphorImager analysis or densitometry. Rad23-HA was detected with HA-specific antibodies (Boehringer Manneheim, Inc.).

UV Irradiation and Survival Measurement

UV irradiation (at 254 nm) and estimation of survival were performed as described previously (Wilcox and Prakash 1981). Irradiated cells were allowed to recover in the dark for 3 days at 30° C.

Cell Cycle Arrest

PolII$^{ts}$: Rad23-HA was expressed in a strain containing a temperature-sensitive allele of RNA polymerase II (RY262: rpb1-1). RY262 expressing Rad23-HA was grown at 23° C. in the presence of 0.1 mM CUSO$_4$ and then diluted 4-fold into YPD (+0.1 mM CuSO$_4$) that was equilibrated at 37° C., and incubated with vigorous aeration for 2 hours. Cells were collected by centrifugation and pulse-chase measurements were performed at 37° C.

Growth arrest with α-factor and hydroxyurea: To measure the stability of Rad23-HA in G$_1$ arrested cells Rad23-HA was expressed in KMY1012, a ura3 derivative of 4910-3-3A (Madura et al. 1990). KMY1012 was grown at 23° C. to A$_{600}$ of approximately 0.3 and then suspended in YPD medium containing 10 ng/ml α-factor (Peninsula Labs). The culture was maintained at 23° C. for 3 hours until greater than 95% of α-factor treated cells were unbudded and arrested in G$_1$. Actively growing JD47-13C cells were treated with 100 μg/ml hydroxyurea (Sigma Chemical Co.) until greater than 75% of the culture displayed large dumbbell shaped cells. The arrested cells were subject to pulse-chase analysis as described earlier.

Rad23 Suppresses N-end Rule Toxicity

Figure 5A:
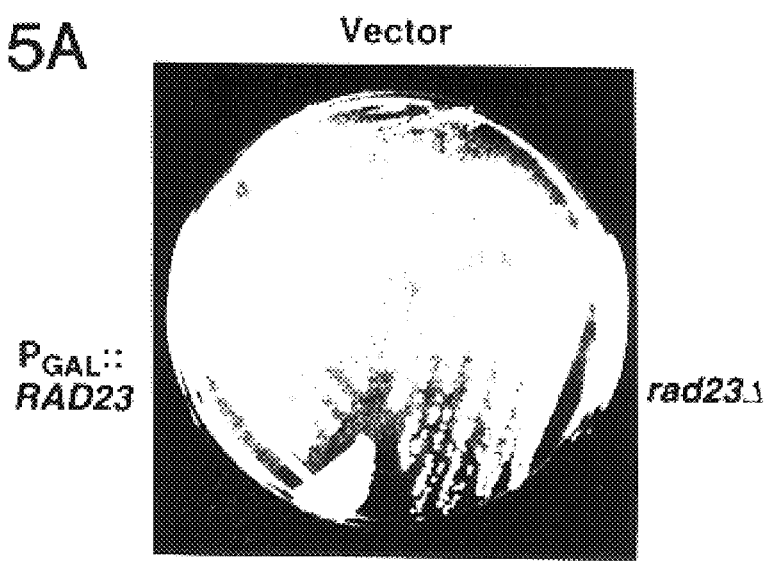
FIGS. 5A and 5B are data showing the genetic interaction between RAD23 and the N-end rule pathway.
Figure 5B:
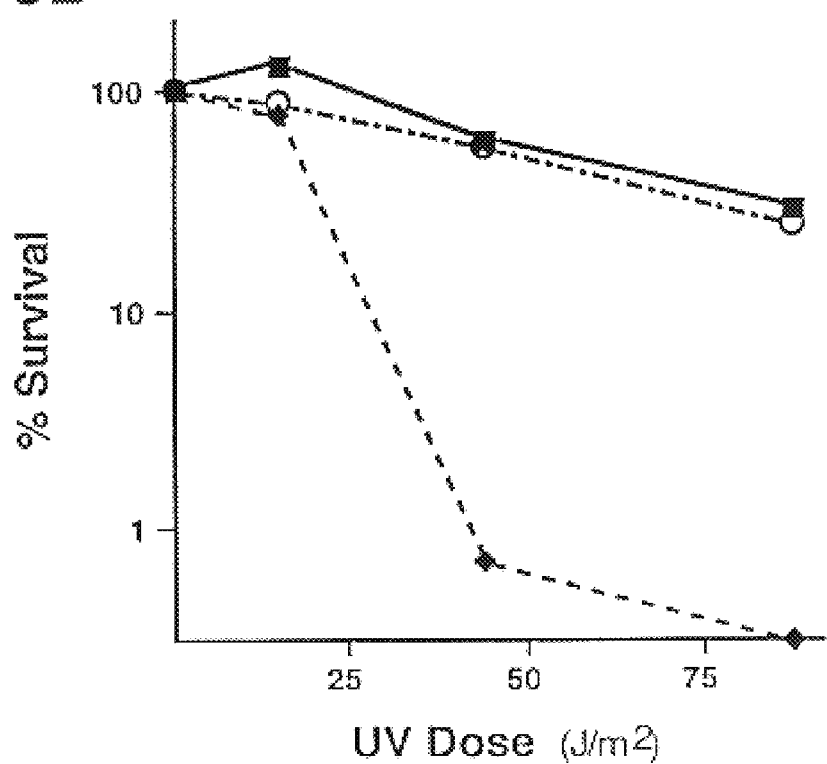
Figure 6A:
FIG. 6A shows that Rad23-HA is unstable in ubc4Δ ubc5Δ suggesting that these E2 proteins do not affect its stability. Rad23-ha is also unstable in N-end rule pathway mutants, ubc2Δ, FIG. 6B and ubr1Δ, shown in FIG. 6C. The stability of Rad23-HA was comparable to that observed in the parental strain (FIG. 7A).
Figure 6B:
FIG. 6 is an autoradiograph showing the results of pulse-labeling experiments which indicate that Rad23-HA is not degraded by Ubc4 or the N-end rule system.
Figure 6C:

Overexpression of the N-end rule pathway causes growth inhibition which stems, at least in part, from the constitutive degradation of the essential Gα protein (Madura and Varshavsky, 1994). The degradation of Gα is believed to activate the mating-response pathway which causes growth arrest in G$_1$. In a screen to identify high-copy suppressors of N-end rule dependent toxicity, RAD23 was isolated. See FIG. 5A. We theorized that Rad23 might interact with the targeting components of the N-end rule pathway and thereby prevent Gα degradation. Such an interaction would suggest that Rad23 is a substrate of the N-end rule pathway, or a regulatory component of this proteolytic system. Two copies of the 9 residue HA epitope were linked to the C-terminus of Rad23. Rad23-HA conferred wildtype levels of UV resistance in rad23Δ, indicating that it is functionally competent. See FIG. 5B. The stability of Rad23-HA was measured by pulse-chase analysis and found to be extremely short-lived in wildtype and ubr1Δ cells indicating that it is not a substrate of the N-end rule pathway, contrary to our prediction. See FIG. 6C. FIG. 6A shows that Rad23-HA is unstable in ubc4Δ ubcΔ suggesting that these E2 proteins do not affect its stability. The degradation of Rad23-ha was also unaffected in ubc2Δ (FIG. 6B), a strain lacking the ubiquitin-conjugating enzyme essential for this proteolytic system. The stability of Gα (and other substrates of the ubiquitin pathway), was unaffected in rad23Δ or when Rad23 was overexpressed (data not shown), demonstrating that Rad23-mediated suppression of N-end rule toxicity does not involve the mating response. Interestingly, it was discovered that rad23Δ also suppressed the toxic effects of N-end rule overexpression, providing genetic evidence for a connection between Rad23 and the proteolytic system (FIG. 5A).

Rad23-HA is Conditionally Degraded

Figure 7A:
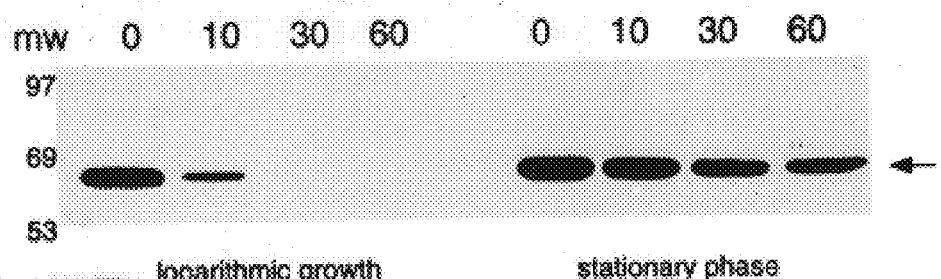
FIGS. 7A–7D are gels showing the growth-stage specific degradation of Rad23-HA.

The data demonstrate that the stability of Rad23-HA varied in a growth-stage dependent manner. The half-life of Rad23-HA exceeded 1 hour in stationary phase cells and was reduced to approximately 1–3 minutes in actively growing cells (FIG. 7A). Even when overexpressed the half-life of Rad23-HA was approximately 1 minute during active growth, attesting to the extraordinary specificity and potency of the degradation apparatus. To exclude the possibility that overall protein degradation was reduced in stationary-phase cells, thereby causing Rad23-HA stabilization, the stability of two distinct classes of substrates of the ubiquitin pathway was examined. Additionally, the in vivo half-life of R-βgal and Ub-P-βgal (substrates of the N-end rule and UFD pathways, respectively) were measured. See FIG. 7D. Unlike Rad23-HA, R-βgal and Ub-P-βgal were efficiently degraded in both exponential and stationary-phases of growth. In contrast M-βgal, which is not recognized as a substrate of the ubiquitin pathway, remained stable in both growth conditions. These results demonstrate that the growth-stage specific degradation of Rad23-HA (and UbL$^{R23}$-βgal, described in FIG. 9B) is highly specific, and is not a reflection of the overall levels of proteolysis.

Figure 7B:
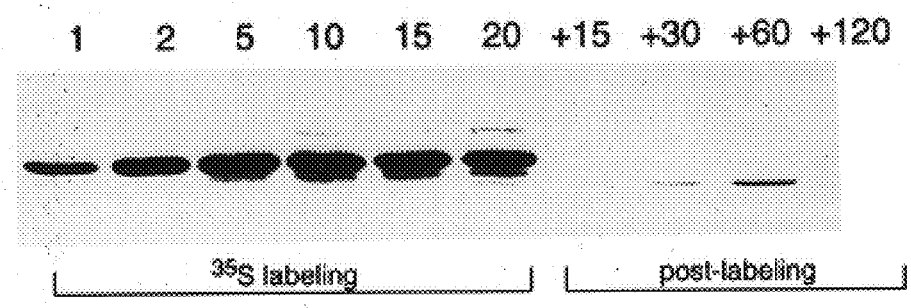

To further characterize the conditions that promote Rad23-HA degradation, stationary-phase yeast cells were radiolabeled to generate high levels of stable Rad23-HA. Rad23-HA was rapidly degraded when these cells were transferred to rich (YPD) medium, and was undetectable within 15 minutes (FIG. 7B). The levels of other proteins were not affected until 60 minutes after transfer (data not shown). The rapid degradation of Rad23-HA precluded our ability to detect multi-ubiquitinated intermediates.

Figure 7C:
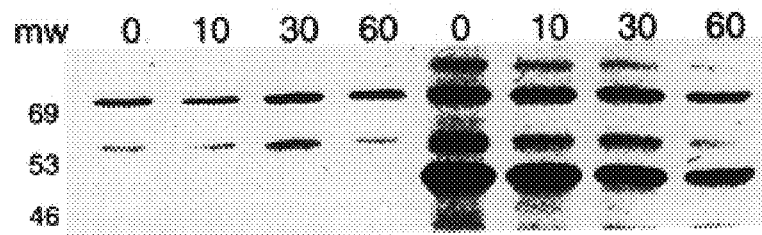
Figure 7D:
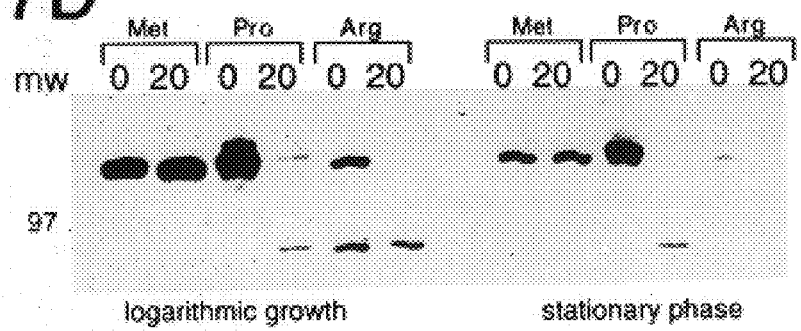
Figure 9A:
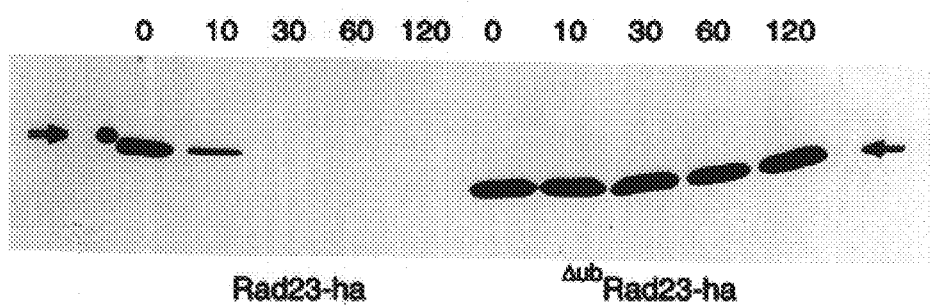
FIGS. 9A and 9B are gels showing that UbL$^{R23}$ is a regulated and portable degradation signal.
Figure 9B:
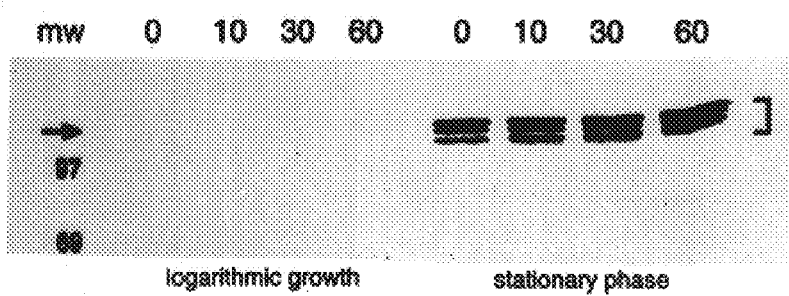

The C-terminal HA epitope does not contribute directly to the destabilization of Rad23-HA because other perturbations of the C-terminus also caused conditional degradation. A Rad23 mutant that lacked 29 C-terminal residues as well as the HA epitope (Rad23$^{1-369}$), displayed extreme instability in logarithmic-phase cells (FIG. 7C), resembling the degradation pattern of both Rad23-HA and UbL$^{R23}$-βgal (FIG. 9B). Significantly, Rad23 $^{1-369}$ conferred UV resistance in rad23Δ (data not shown), suggesting that the function of Rad23 in mediating protein degradation is restricted to stationary-phase cells.

Transient Cell-cycle Arrest Does Not Affect Rad23-HA Stability

The growth-stage dependent degradation of Rad23-HA prompted the examination of its stability during the cell-cycle. The growth of exponential stage cultures was arrested with α-factor (Madura and Prakash, 1990) or hydroxyurea (Sanchez et al., 1996), and Rad23-HA stability was determined. Pulse-chase studies revealed that Rad23-HA was efficiently degraded in these growth arrested cells (FIGS. 8B and 8C). Also a temperature-sensitive allele of RNA Pol II was employed to asynchronously arrest growth of an actively propagating culture (Nonet et al., 1987). The data show that Rad23-HA remained extremely short-lived (FIG. 8A). We conclude from these results that the degradation of Rad23-HA is not affected by transient growth arrest of exponential-phase cells.

The Ubiquitin-like Domain is Required for Rad23-HA Degradation

Ubiquitin is expressed either as an N-terminal fusion to specific ribosomal proteins (Finley et al., 1989), or as a chain of tandemly-linked Ub multimers (Ozkaynak et al., 1990). The C-terminus of Ub is important for its processing, activation and conjugation to cellular proteins. The C-terminal residues in most ubiquitin-like domains differ from that of Ub suggesting that they are generally not excised and conjugated to other proteins.

Varshavsky and colleagues found that the expression of Ub as a non-cleavable extension on β-galactosidase led to extreme instability of the fusion protein following subsequent conjugation to a multi-ubiquitin chain (Johnson et al. 1992). Since $UbL^{R23}$ is retained in mature Rad23, its role in Rad23-HA degradation was investigated by constructing a mutant that lacked this motif ($^{\Delta UbL}$Rad23-HA). We found that $^{\Delta UbL}$Rad23-HA was stable in actively growing cells (FIG. 9A), displaying a half-life that exceeded 10 hours during exponential growth. Significantly, $^{\Delta UbL}$Rad23-HA failed to complement the UV sensitivity of rad23Δ (Watkins et al. 1993), suggesting that $UbL^{R23}$ may have a proteolytic function in DNA repair.

The Ubiquitin-like Domain is An Autonomous Degradation Signal

The ability of $UbL^{R23}$ to promote the degradation of a reporter protein was tested by linking it to β-galactosidase ($UbL^{R23}$βgal). The data illustrate that $UbL^{R23}$-βgal is stable in stationary-phase but exceedingly unstable during active growth (FIG. 9A and FIG. 9B), intensifying the degradation pattern of Rad23-HA (FIG. 7A). Long over-exposures of the autoradiograms revealed a low level of $UbL^{R23}$-βgal in the 0 min sample in logarithmically growing cells, and quantitative β-galactosidase activity measurements confirmed these findings (data not shown). These results demonstrate that $UbL^{R23}$ is both necessary and sufficient for the targeting and degradation of Rad23-HA, and is predicted to contain amino acid residues that are recognized by proteolytic factors. Furthermore, $UbL^{R23}$ contains sequences that are sensitive to regulatory signals because $UbL^{R23}$-βgal mimicked the regulated degradation of Rad23-HA. $UbL^{R23}$-βgal migrated as a set of 3 closely spaced electrophoretic bands. It is not known if these bands correspond to multiubiquitination or other modifications of UbL R23gal.

The Ubiquitin Fusion Degradation (UFD) Pathway is Involved In the Degradation of Rad23-HA The placement of ubiquitin on the N-terminus of a protein such as β-galactosidase (Ub-P-βgal), can promote degradation by the Ubc4 ubiquitin-conjugating enzyme (Bachmair et al., 1986). Ubc4 assembles a multiubiquitin chain at a conserved lysine in the Ub extension of Ub-P-βgal (Johnson et al., 1992). Since the lysine residues which serve as attachment sites for the formation of a multiubiquitin chain are conserved between Ub and $UbL^{R23}$, we predicted that Rad23-HA might also be targeted by Ubc4. Ubc5 encodes another ubiquitin-conjugating enzyme which is approximately 90% identical to Ubc4 and is believed to have overlapping substrate specificity (Seufert and Jentsch, 1990). Rad23-HA stability was examined in ubc4Δ ubc5Δ. In these cells, degradation of the protein was unaffected (FIG. 6A) compared to the wildtype strain (data not shown). These findings show that this class of E2 enzymes does not target Rad23-HA for degradation.

Figure 10A:
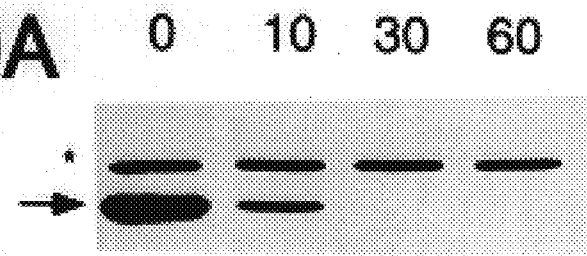
FIGS. 10A–10E show that Ufd5 is required for the degradation of Rad23-HA. Rad23-HA was expressed in a set of strains bearing mutations in ufd1-5. In vivo stability was measured by pulse-chase methods and quantitated by PhosphorImager. Only ufd5Δ was found to be important for Rad23-HA degradation. An antibody cross-reacting band (*) served as a useful internal control for loading.
Figure 10B:
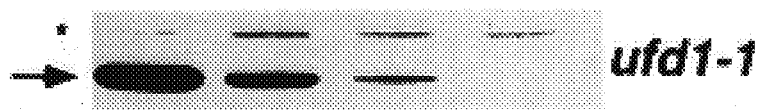
Figure 10C:
Figure 10D:
Figure 10E:

In a search for factors that affect the degradation of Ub-P-βgal Johnson, et al. performed a genetic screen and identified a class of mutants (termed the UFD pathway- for ubiquitin fusion degradation pathway) that differentially affected Ub-P-βgal stability. Johnson et al. determined that UFD5 was the only UFD pathway gene that was also required for the degradation of N-end rule substrates, which are distinct from Ub-P-βgal. While N-end rule substrates are ubiquitinated by Ubc2 and Ubr1, Ub-P-βgal is ubiquitinated by Ubc4. The possibility that the ufd mutants might affect the stability of Rad23-HA was examined. Pulse-chase measurements showed that Rad23-HA was strongly stabilized in ufd5Δ (FIG. 10E), but not in ufd1–ufd4 (FIGS. 10B–10D). Multiubiquitinated derivatives of Ub-P-βgal were detected in ufd5Δ, while Rad23-HA accumulated as an apparently unmodified protein. Although the biochemical activity of Ufd5 is unknown, these results demonstrate that the channeling of substrates to the proteasome can follow diverse routes. This observation is also supported by our finding that different proteasome mutants have distinct effects on Rad23-HA stability (see below).

Proteasome Dependent Degradation of Rad23-HA

Substrates of the Ub system are generally degraded by the 26S proteasome, an evolutionarily conserved structure of >2×106 Daltons. It was recently reported that a yeast pheromone-specific receptor, Ste2, is ubiquitinated but degraded in the vacuole in a proteasome-independent manner (Hicke and Riezman 1996). In contrast ornithine decarboxylase (ODC) is degraded by the 26S proteasome, although it is not ubiquitinated (Tokunage et al. 1994). Given these exceptions, to the generally accepted model for targeting and degradation of ubiquitinated substrates, we measured the stability of Rad23-HA in yeast strains bearing mutations in either proteasome subunits or vacuolar proteases, to determine if its degradation involved the ubiquitin/proteasome pathway. Cim5 is an ATPase subunit of the 19S regulatory complex of the 26S proteasome and is required for the degradation of Ub-P-βgal (Ghislain et al. 1993). The stability of Rad23-HA in exponential-stage cim5-1 cells was measured and the results show that it was very stable ($t_{1/2}$ >10 hrs, FIG. 11B). Pre1 and Pre2 are subunits of the 20S catalytic core of the 26S proteasome, and mutants are sporulation defective and stress-sensitive. In agreement with the results observed in cim5-1, we found that Rad23-HA was stabilized in actively growing pre1-1 pre2-2 cells ($t_{1/2}$~1 hr, FIG. 11A). In contrast the degradation Rad23-HA was unaffected in pep4Δ prb1-Δ1, which is defective in vacuolar proteolysis ((Hicke and Riezman 1996), FIG. 11E. Thus, it appears that Rad23-HA degradation requires the 26S proteasome.

The very rapid degradation of Rad23-HA precluded detection of multiubiquitin intermediates. Ubiquitinated Rad23 was previously detected (Watkins et al. 1993), suggesting that Rad23-HA degradation is ubiquitin-mediated. Mcb1 is a yeast counterpart of the human S5a protein which encodes a multiubiquitin-chain binding protein of the 26S proteasome. The stability of Rad23-HA was tested in mcb1Δ and results demonstrated that it continued to be degraded rapidly (FIG. 11D). Since mcb1Δ stabilizes only a subset of ubiquitinated substrates in yeast cells it is possible that other multiubiquitin-chain binding proteins can mediate Rad23-HA degradation. The stability of Rad23-HA in doa4Δ-1, an isopeptidase associated with the 26S proteasome, was also measured since many substrates of the ubiquitin system are stabilized in this mutant. Surprisingly, Rad23-HA continued to be degraded in doa4Δ-1 (FIG. 11C). These results demonstrate that substrates of the ubiquitin system can follow diverse routes into the proteasome.

Rad23 Interacts With Other Components of the Proteasome

Rad23 was linked to lexA and interacting factors were sought by the 2-hybrid method (Paetkau et al. 1994). We identified Irt1 (interaction with Rad23), a protein whose C-terminal domain displays significant homology with the 26S subunit Yta6 (FIG. 8A, Schnall et al. 1994) and Cim3 and Cim5. See FIG. 12A. The large N-terminal domain of Irt1Δ is not similar to any known polypeptide sequence. The degradation of Rad23-HA was unaffected in irt1Δ (data not shown), indicating that the interaction between Rad23 and Irt1 is likely to be of a regulatory nature.

Figure 12B:
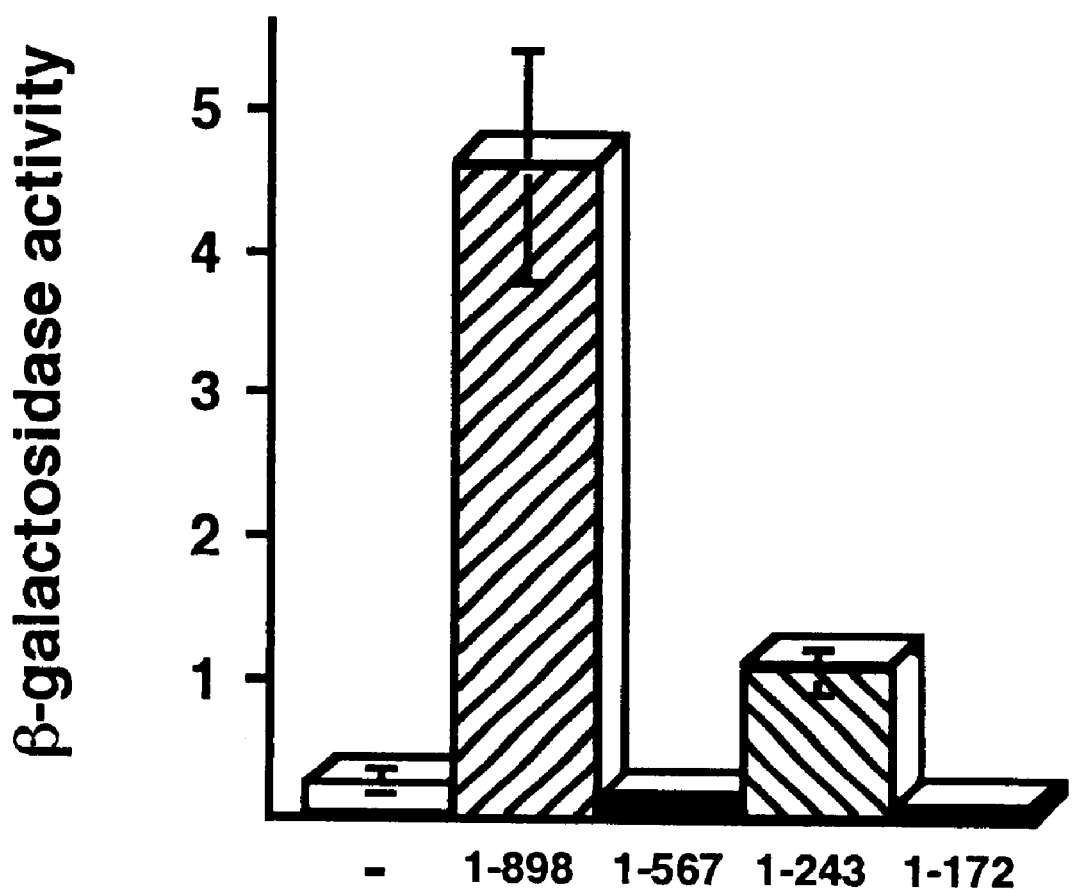

To further characterize the interaction between Rad23 and Irt1 several deletion derivatives of Irt1 were constructed and tested for their ability to interact with Rad23 (FIG. 12B). Full-length Irt1 (897 amino acids) as well as three C-terminal deletion variants, comprising residues 1-567, 1-243 and 1-172, were tested in the 2-hybrid system. Irt1$^{1-567}$ lacks the highly conserved ATPase domain located in the C-terminus, while the larger truncations removed additional residues of unknown function.

EXAMPLE III

Ubiquitin-like Sequences Are Proteasome Interacting Domains

A family of proteins that contain ubiquitin-like sequences (UbL's) has been identified in diverse organisms (Garrett et al., 1995; Shen et al., 1996). Some UbL's are post-translationally conjugated to other proteins in a mechanism similar to that described for ubiquitin-conjugation (Johnson et al., 1997; Mahajan et al., 1997). However, a distinct class of UbL's are retained in the original translational product and not conjugated to other proteins (Watkins et al., 1993). The proteins to which these UbL's are fused share little in common and offer no obvious clues to their biological functions. Furthermore, the effect of a UbL on the activities of the protein to which it is linked is unknown. Although UbL's display no more than 20–30% identity to the amino acid sequence of ubiquitin, their 3-dimensional structures are predicted to be highly similar (van der Spek et al., 1996). The two proteins in yeast that contain N-terminal ubiquitin-like domains were reported to be stable (Biggins et al., 1996). However, we have determined that Rad23 is ubiquitinated and degraded during the G1/S-phase transition of the cell-cycle. The fusion of ubiquitin to the N-terminus of β-galactosidase (Ub-Pro-βgal) has also been shown to cause rapid degradation by the ubiquitin pathway (Johnson et al., 1995; Bachmair et al., 1986).

Dsk2 is another yeast protein that contains a ubiquitin-like domain (UbL$^{DSK}$), and deletion of both genes (rad23 dsk2) causes a temperature sensitive growth defect (15), suggesting that their activities converge at some unknown biochemical level.

To examine if Rad23 associated with proteolytic factors we linked Rad23 and UbL$^{R23}$ to GST and found that both GST-Rad23 and GST-UbL$^{R23}$ formed stable interactions with the 26S proteasome. See Example I. The data presented herein demonstrate that proteasome-interaction is a feature shared by other members of the family of ubiquitin-like proteins, and indicate that UbL containing proteins mediate proteolytic functions. UbL's and UbL-containing proteins have been implicated in many biological pathways including DNA repair (Watkins et al., 1993), spindle pole-body duplication (Biggins et al., 1996), transcription elongation (Garrett et al., 1995), von Hipple Landau syndrome (Kibel et al., 1995) and nuclear/RNA transport (Mahajan et al., 1997). The best characterized among these proteins is yeast Rad23.

The findings presented indicate that UbL/proteasome interaction is regulated. The UbL from yeast Dsk2 (UbL$^{DSK}$) interacts with the proteasome preferentially in actively growing cells. Overexpression of UbL$^{R23}$ inhibits the degradation of specific substrates of the ubiquitin pathway perhaps by saturating the proteasome targeting pathway. Significantly, our results show that UbL-linked proteins interact with the proteasome without prior attachment to a multiubiquitin chain, defining a novel mechanism for targeting proteins to the proteasome.

Materials and Methods for Example III

Strains and Extracts

The yeast strains used in these studies were derived from JD47-13C; MATahis3-Δ200trpl-Δ63 lys2-801 ura3-52 leu2-2, 112 (J. Dohmen). Rad23 deletion (CSY85; rad23Δ::URA3) was made in JD47-13C using pDG28. Extracts for immunoprecipitations and affinity purified purification were described previously. (Schauber et al., 1998).

Reagents

Proteasome inhibitors were obtained from Calbiochem, glutathione-Sepharose from Pharmacia, anti-ubiquitin antibodies from Sigma, and anti-βgalactosidase antibodies from Promega.

Plasmids and Constructs

UBL's and CIM5 were amplified by PCR with oligonucleotides containing a 5' NcoI and 3' KpnI restriction site and ligated into similarly treated pCBGST1 (Schauber et al., 1998). The expression of the proteins was induced with 0.15 mM CUSO$_4$. Plasmids encoding Pre-1-FLAG and Sen3-HA were provided by J. Dohmen and M. Hochstrasser.

Figure 13A:
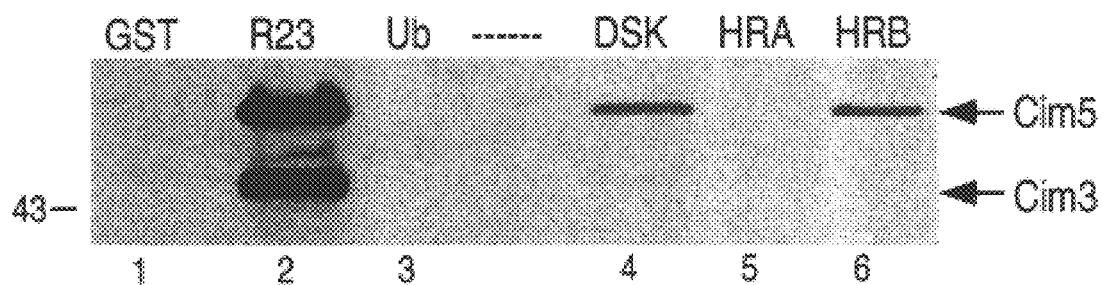
FIGS. 13A and 13B are gels showing that UbL's from different sources interact with the proteasome. GST linked proteins were expressed in yeast and purified on glutathione-Sepharose. Proteins retained on the beads were resolved in SDS-polyacrylamide gels, transferred to nitrocellulose, and incubated with antisera specific to proteasome subunits Cim3 and Cim5. The blot was developed by enhanced chemiluminescence (Amersham).
Figure 14A:
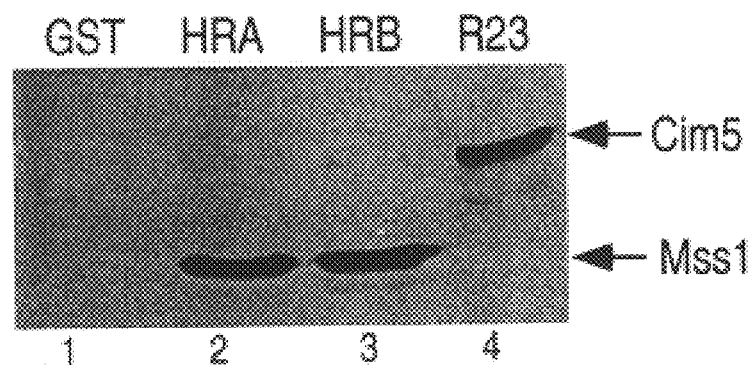
FIGS. 14A and 14B are a series of blots showing that UbL's interact with the 19S/PA700 complex.

UbL's are proteasome-interacting sequences. The ubiquitin-like domains of yeast Rad23 and Dsk2, and human HHR23A and -B, were linked to the C-terminus of glutathione S-transferase (GST), and expressed in yeast. Extracts were incubated with glutathione-Sepharose, and bound proteins separated in a SDS-polyacrylamide gel, transferred to nitrocellulose and analyzed by immunological methods. The blot was incubated with Cim3 and Cim5 antibodies, which recognize subunits of the 26S proteasome, and a strong interaction was detected in the beads containing GST-UbL$^{R23}$. See FIG. 13A, lane 2. UbL$^{R23}$/proteasome interaction was resistant to 1M NaCl, and treatment with detergents including 1% Triton X-100, 0.5% NP40 and 0.1% SDS (data not shown). Ubiquitin (GST-Ub) did not interact appreciably with the 26S proteasome (FIG. 13A, lane 3), supporting the idea that ubiquitin is recognized by the proteasome only when it is assembled into a multiubiquitin chain (Chau et al., 1989). In contrast, the UbL may have evolved to specifically interact with the proteasome without prior attachment to a multiubiquitin chain. Weaker interactions were detected with GST-UbL$^{Dsk}$ and GST-UbL$^{HRB}$ (lanes 4 and 6), but not with GST-UbL$^{HRA}$ (lane 5). To examine the possibility that GST-UbL$^{HRA}$ and CST-UbL$^{HRB}$ might interact more favourably with human proteins we incubated Hela cell S100 extracts with GST-UbL$^{HRA}$ and GST-UbL$^{HRB}$. The interacting proteins were analyzed in a western blot with Cim5 antibodies which crossreact with Mss1, a human counterpart of yeast Cim5 (Ghislain et al., 1993). Mss1 was detected in GST-UbL$^{HRA}$ and GST-Ubl$^{HRB}$ beads (FIG. 14A, lanes 2 and 3), but not GST (lane 1). A control lane containing GST-UbL$^{R23}$interacting proteins showed that the antibody reaction against Cim5 was efficient (FIG. 14A, lane 4). In agreement with these findings we found that cells expressing Sen3-HA, a non-ATPase 19S subunit (DeMarini et al., 1995), also interacted with GST-UbL$^{R23}$ but not GST (see FIG. 14A).

Figure 13B:
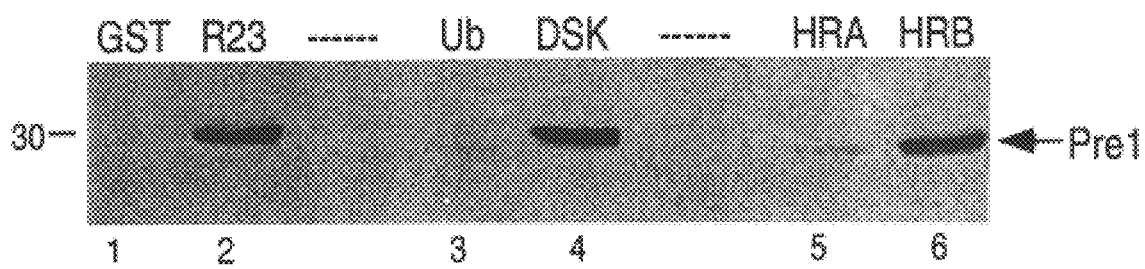

Consistent with these results, we detected Pre1-FLAG (an epitope-tagged 20S subunit) in beads containing GST-UbL$^{R23}$, GST-UbL$^{DsK}$, and GST-UbL$^{HRB}$ (FIG. 13B). These results show that several different subunits of the 19S and 20S components of the 26S proteasome can be detected in a complex that interacts with ubiquitin-like domains. We conclude that a common biochemical property of a UbL is its interaction with catalytically active 26S proteasome.

Figure 14B:
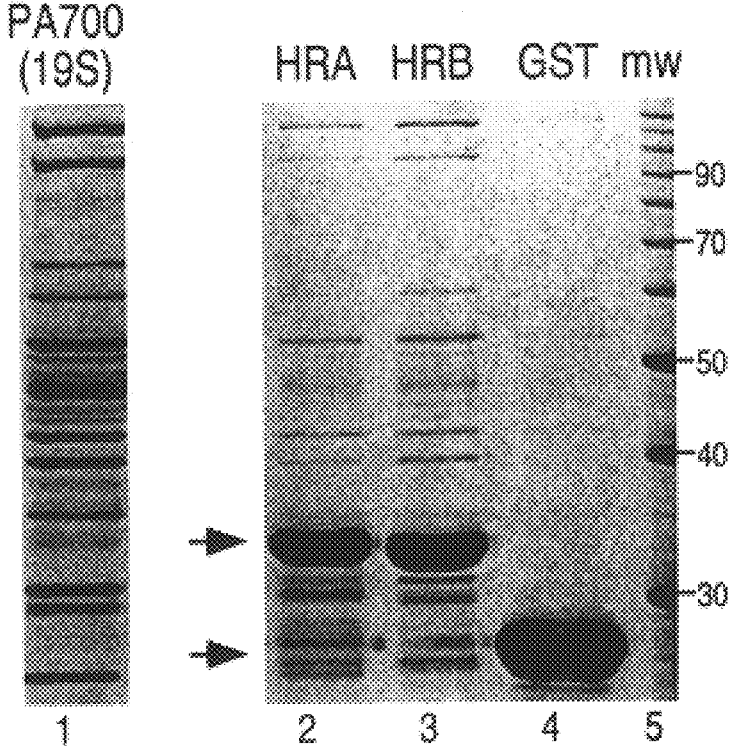

UbL's interact with the 19S regulatory component of the 26S proteasome. Based on the activities associated with UbL$^{R23}$, the proteasome interacting-subunit could be located in either the 19S or 20S complexes. To examine the interaction with the 19S regulatory complex GST-UbL$^{HRA}$ and GST-UbL$^{HRB}$ were incubated with approximately 5µg 19S/PA700 (a gift from Dr. G. DeMartino, Univ. of Texas, Dallas, Tex.), for 10 hr at 4° C. Bound proteins were resolved in SDS-PAGE and examined by silver staining. A significant fraction of the input protein was detected in the beads containing UbL$^{HRA}$ and UbL$^{HRB}$ (FIG. 14B, lanes 2 and 3). The profile of 19S/PA700 subunits that bound GST-UbL$^{HRA}$ and GST-UbL$^{HRB}$ was similar demonstrating that the entire complex, rather than specific subunits, interacts with the UbL. UbL$^{HRB}$, but not UbL$^{HRA}$, showed detectable interaction with yeast proteasomes, although both chimeras bound human proteasome (FIG. 14). This variance in interaction may result from subtle differences in their sequences, which might offer clues to the residues that are important for proteasome binding.

A novel mechanism is involved in UbL$^{R23}$/proteasome interaction. Substrates of the ubiquitin system are covalently linked to a multiubiquitin chain prior to recognition by the 26S proteasome. In a search for multiubiquitin-chain binding proteins van Nocker et al., identified Mcb1, which is a component of the 19S regulatory complex of the proteasome (van Nocker et al., 1996). Since UbL's interact with the proteasome through the 19S complex (FIG. 14B), we investigated if UbL$^{R23}$ could interact with the proteasome in mcb1Δ. We purified GST-UbL$^{R23}$ from mcb1Δ and found that it co-precipitated Cim5 and Cim3, demonstrating that its interaction with the proteasome is not mediated by Mcb1. This result proves that there are alternate ways for substrates and regulators to interact with the proteasome, and is consistent with studies which showed that some substrates of the ubiquitin system are efficiently degraded in mcb1Δ (van Nocker et al., 1996).

Figure 15:
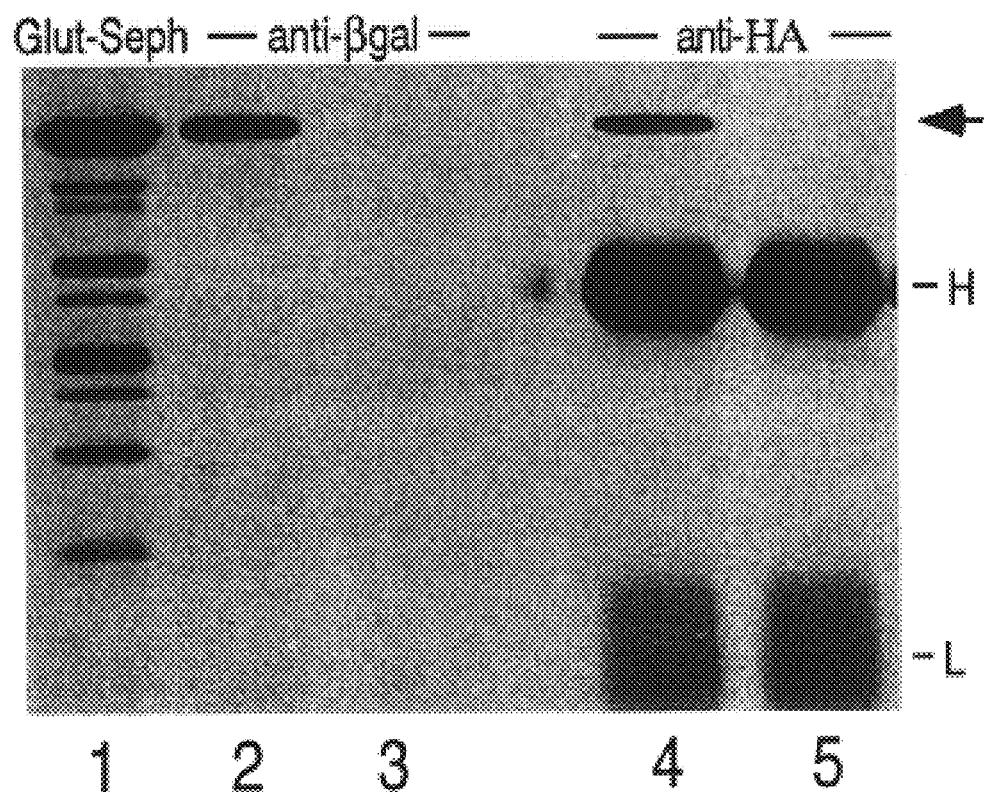
FIG. 15 is a gel showing that UbL$^{R23}$ can target heterologous proteins to the proteasome. UbL$^{R23}$ was linked to β-galactosidase and Ura3-HA and transformed into yeast cells expressing GST-Cim5. Lane 1 contains affinity purified GST-Cim5. UbL$^{R23}$-βgal was immunopurified with anti-βgalactosidase antibodies and GST-Cim5 was co-purified (lane 2). An extract containing only GST-Cim5 was treated with anti-β galactosidase antibodies (lane 3). UbL$^{R23}$-Ura3-HA was precipitated with anti-HA antibodies and GST-Cim5 was co-purified (lane 4). An extract containing only GST-Cim5 was incubated with anti-HA antibodies and resolved as a negative control (lane 5). The blot was developed with anti-GST antibodies. (H and L indicate the positions of immunoglobulin heavy- and light-chains from the HA immunoprecipitation).

UbL$^{R23}$ can target heterologous proteins to the proteasome. UbL$^{R23}$ was linked to the N-terminus of β-galactosidase (UbL$^{R23}$-βgal) and Ura3-HA (UbL$^{R23}$-Ura3-HA), and the plasmids were transformed into a yeast strain expressing GST-Cim5. Extracts were incubated with anti-β-galactosidase or anti-HA antibodies, and immunoprecipated protein recovered on Protein-A Sepharose beads, resolved in SDS-PAGE and transferred to nitrocellulose. The nitrocellulose filter was incubated with anti-GST antibodies, and the position of full-length GST-Cim5 from a control extract, is indicated by the arrow (FIG. 15, lane 1). We found that GST-Cim5 was highly susceptible to proteolysis (as indicated by the large number of smaller fragments). Extracts containing GST-Cim5 and UbL$^{R23}$-βgal were incubated with anti-β-galactosidase, and a strong reaction against GST-Cim5 was detected in the immunoprecipitates (FIG. 15, lane 2). Interestingly, the degradation products of GST-Cim5 (lane 1), were not seen in lane 2 suggesting that only intact GST-Cim5 is incorporated into the proteasome. Extracts containing only GST-Cim5 were also incubated with anti-βgal antibodies and resolved on the gel. As expected, GST-Cim5 was not precipitated in this reaction (FIG. 15, lane 3). To extend these findings further we examined if UbL$^{R23}$-Ura3-HA could also selectively precipitate GST-Cim5. A band consistent with GST-Cim5 was detected (lane 4), and as observed in lane 3 only intact GST-Cim5 protein was precipitated with UbL$^{R23}$-Ura3-HA. An extract containing only GST-Cim5 was reacted with anti-HA antibodies and GST-Cim5 was not precipitated (lane 5). We conclude that UbL$^{R23}$ is an autonomous sequence that can target unrelated proteins to the proteasome.

UbL/proteasome interaction can be regulated. We found that UbL$^{DSK}$ forms a weak association with the proteasome. The function of Dsk2 is expected to be confined to actively growing cells because it is required for spindle pole-body duplication. Our preliminary studies indicate that UbL$^{DSK}$ interacts more favorably with the proteasome in actively growing cells. It remains to be determined how the natural C-terminal extension regulates UbL/proteasome interaction. We have reported in Example I that specific alleles of Rad23 are rapidly degraded by the ubiquitin/proteasome pathway, in a mechanism that requires UbL$^{R23}$. Since these Rad23 variants are degraded only in actively growing cells, it appears that UbL$^{R23}$/proteasome interaction may also be regulated.

Figure 16A:
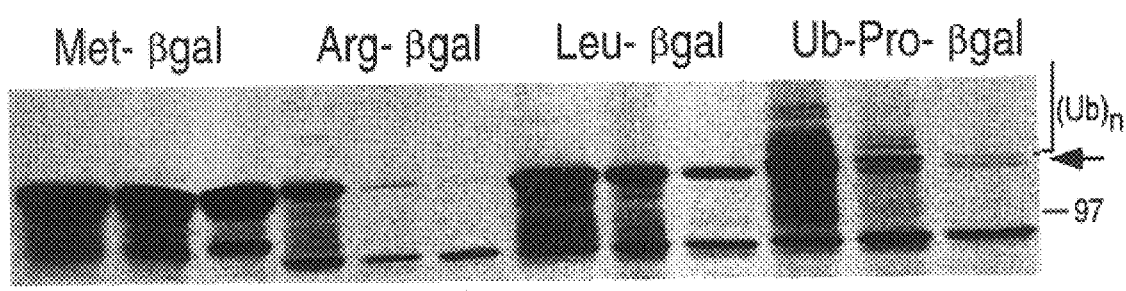
FIGS. 16A and 16B are a pair of gels illustrating that UbL$^{R23}$ interferes with the degradation of specific substrates. Yeast cells expressing a test protein Met-βgal, or substrates of the N-end rule (Arg-βgal and Leu-βgal) and UFD pathway (Ub-Pro-βgal) were transformed with plasmids expressing GST or GST-UbL$^{R23}$. The stability of the proteins was determined by $^{35}$S-pulse-chase methods. Samples were analyzed after 0, 10 and 60 min in Chase medium containing cycloheximide. The precipitated proteins were separated by SDS-PAGE and the fluorograms exposed to X-ray film. This figure reproduces a dark exposure of the gel to reveal high molecular-weight derivatives of Leu-βgal and Ub-Pro-βgal (indicated as (Ub)n) in cells expressing GST-UbL$^{R23}$.
Figure 16B:
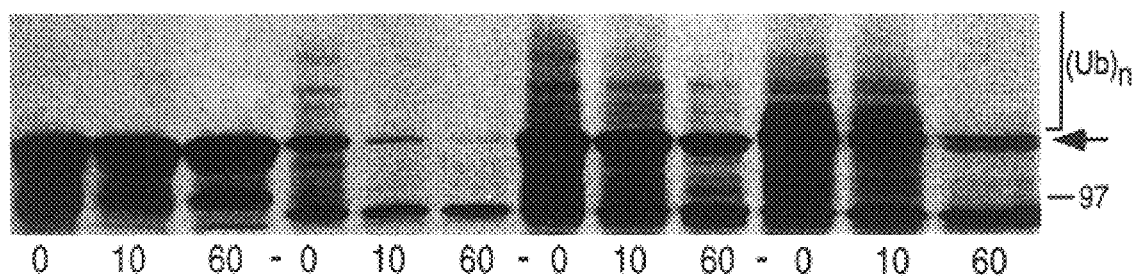

UbL$^{R23}$ interferes with proteasome function. The high affinity interaction between UbL$^{R23}$ and the 26S proteasome suggested that it might affect the degradation of substrates of the ubiquitin system. We examined the stability of substrates of the N-end rule (Arg-βgal and Leu-βgal) and UFD pathways (Ub-Pro-βgal), by measuring β-galactosidase activity of test substrates. The levels of Leu-βgal and Ub-Pro-βgal were 2-3 fold higher in cells expressing GST-UbL$^{R23}$, than in the GST control. In contrast, the activity in cells expressing Met-βgal and Arg-βgal was unchanged (data not shown). To confirm these results we measured the in vivo half-lives of test substrates by pulse-chase analysis. We found that Leu-βgal and Ub-Pro-βgal were moderately stabilized in cells expressing GST-UbL$^{R23}$ (FIG. 16B), as compared to GST (FIG. 16A). These results are in agreement with the β-galactosidase activity measurements. Significantly, ubiquitinated derivatives of Leu-βgal and Ub-Pro-βgal accumulated in cells expressing GST-UbL$^{R23}$, indicating that UbL$^{R23}$ interferes with a post-targeting step in substrate degradation. This effect is most easily seen in Leu-βgal levels at the 0 time-point. These results suggest that UbL$^{R23}$ interaction with the proteasome can block, or otherwise interfere with, the access of specific substrates to the proteasome. The alternate possibility that GST-UbL$^{R23}$ increased ubiquitin-conjugation is considered less likely because the rate of Leu-βgal degradation was reduced, and not increased as would be expected if it was more efficiently targeted. In contrast to the stabilization of Leu-βgal, Arg-βgal remained extremely unstable in strains expressing either GST or GST-UbL$^{R23}$. This result suggests that the fate of Type I (Arg-βgal) and Type II (Leu-βgal) substrates of the N-end rule pathway may diverge following their conjugation to ubiquitin by the targeting components Ubr1/Ubc2).

The function of ubiquitin-like domains (UbL) was previously unknown. We report here that the UbL is a cis-acting signal that can translocate UbL-linked proteins to the proteasome. In addition to the Rad23 proteins and Dsk2, we also examined the interaction between Elongin-B and the proteasome. Consistent with the findings shown in FIG. 13, we detected an interaction with Cim5 (data not shown). Elongin B is a UbL-containing protein that forms a heterotrimeric complex which modulates transcription by RNA Pol II. We have also reported elsewhere that UbL$^{R23}$ can function as a portable degradation signal, when fused to the N-terminus of β-galactosidase (UbL$^{R23}$-βgal). Although the biological significance of UbL/proteasome interaction is unknown, we suggest that UbL's can be either substrates or regulators of the proteasome. There also exists an interesting possibility that a UbL-linked protein can promote the degradation of other proteins in trans, by binding and transporting them to the proteasome. A particular advantage of this mechanism for proteasome targeting is that an elaborate ubiquitin-dependent apparatus is dispensed with, and the in vivo levels of a substrate could be regulated by the concentration of its cognate UbL-containing partner, and its affinity for the proteasome. A precedent for this mechanism is noted by the (ubiquitin-independent) antizyme-mediated degradation of ornithine decarboxylase by the proteasome (Murakami, et al., 1992). A potential target for Rad23-mediated degradation could be Rad4, to which it binds with high affinity. Rad23 and Rad4 are both important for the assembly of the nucleotide excision repair complex, and genetic and biochemical studies have implicated a regulatory role for Rad23. We have shown that Rad23 and Rad4 can be purified in a complex with the proteasome, although it remains to be determined if Rad23 influences Rad4 stability. The Rad23-mediated link between DNA repair and protein degradation may define a mechanism to recycle the repair complex, or to facilitate recovery after the completion of DNA repair.

Of the four UbL's present in yeast, only Smt3 and Rub1 are conjugated post-translationally to other proteins. A mammalian counterpart of Smt3 (SUMO) is covalently linked to RanGAP1, although this modification does not appear to promote degradation. However, it is possible that only a small fraction of RanGAP1 is post-translationally modified, and its SUMO-mediated turnover may be masked by the large fraction of unmodified RanGAP1. We showed in FIG. 13 that mono-ubiquitin (GST-Ub) failed to interact with the proteasome. Since ubiquitin interacts with the proteasome only when it is assembled into a multiubiquitin chain, we propose that substrate-linked Smt3 and substrate-linked Rub1 might also be targeted to the proteasome. This idea can be tested once the physiological targets of Smt3 and Rub1 are identified.

UbL-containing proteins may prevent the degradation of other proteins by blocking their access to proteolytic factors. For instance, GST-UbL$^{R23}$ interaction with the proteasome inhibited the degradation of specific substrates of the ubiquitin pathway (FIG. 16). We found that UbL$^{R23}$ stabilized Leu-βgal but not Arg-βgal, which are distinct substrates of the N-end rule pathway.

UbL$^{R23}$ also stabilized Ub-Pro-βgal, a substrate of the UFD pathway. Pulse-chase experiments suggested that inhibition of degradation occurred at a post-targeting step because multi-ubiquitinated derivatives of Leu-βgal and Ub-Pro-βgal accumulated in the presence of GST-UbL$^{R23}$.

Rad23 and Dsk2 are the only yeast proteins that retain ubiquitin-like domains in the mature proteins. Rad23 is required for nucleotide excision repair, while Dsk2 is involved in spindle pole-body (SPB) duplication. Deletion of both genes (rad23 dsk2) causes a temperature sensitive growth defect indicating that the biochemical activities of Rad23 and Dsk2 intersect, possibly at the level of the 26S proteasome. UbL$^{R23,}$ but not UbL$^{DSK}$, interferes with the degradation of specific test proteins. We suggest that substrates of the N-end rule and UFD pathway may be channeled to a specific proteasome isoform that is recognized only by UbL$^{R23}$. Interestingly, UbL$^{DSK}$/proteasome interaction is enhanced in actively growing cells, also suggesting that compositionally distinct types of proteasomes may regulate UbL interactors. This observation is consistent with a previous study which showed that specific 20S proteasome subunits are replaced following γ-interferon treatment in mammalian cells (Gaczynska, et al., 1993).

EXAMPLE IV

Figure 17:
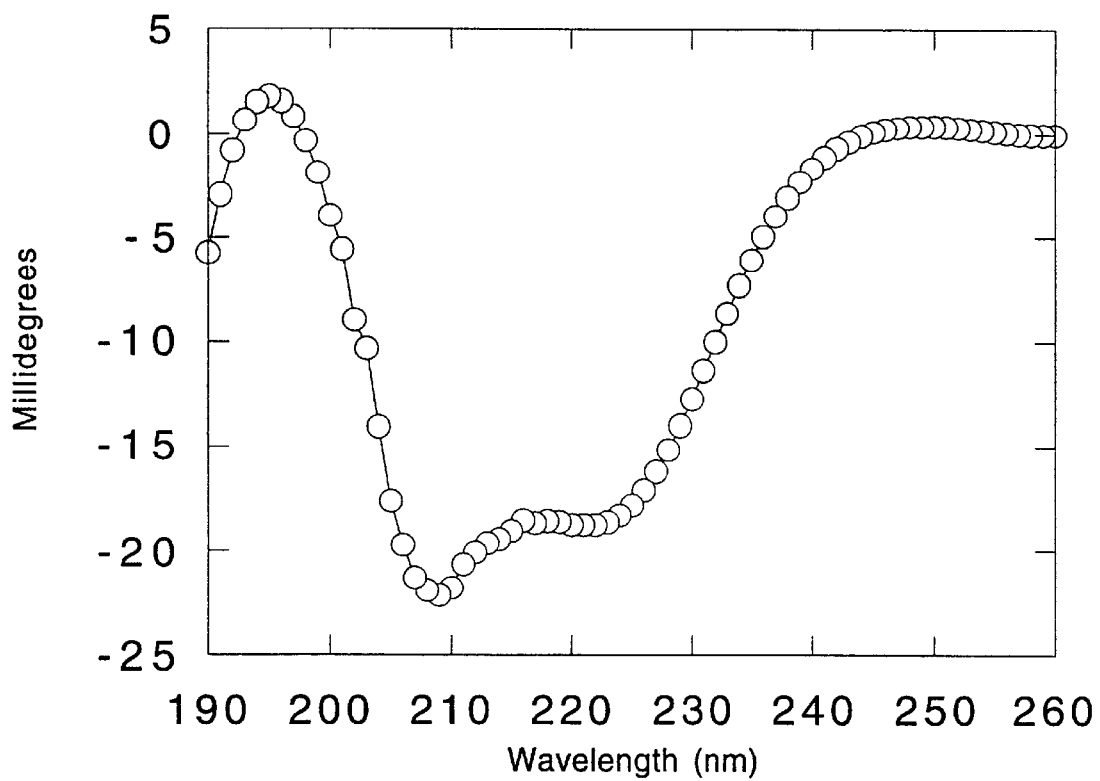
FIG. 17 is a graph showing the CD spectra of Rad23. The data show the spectra of a typical globular protein. The CD spectra of the protein is not altered by heating (not shown).
Figure 18:
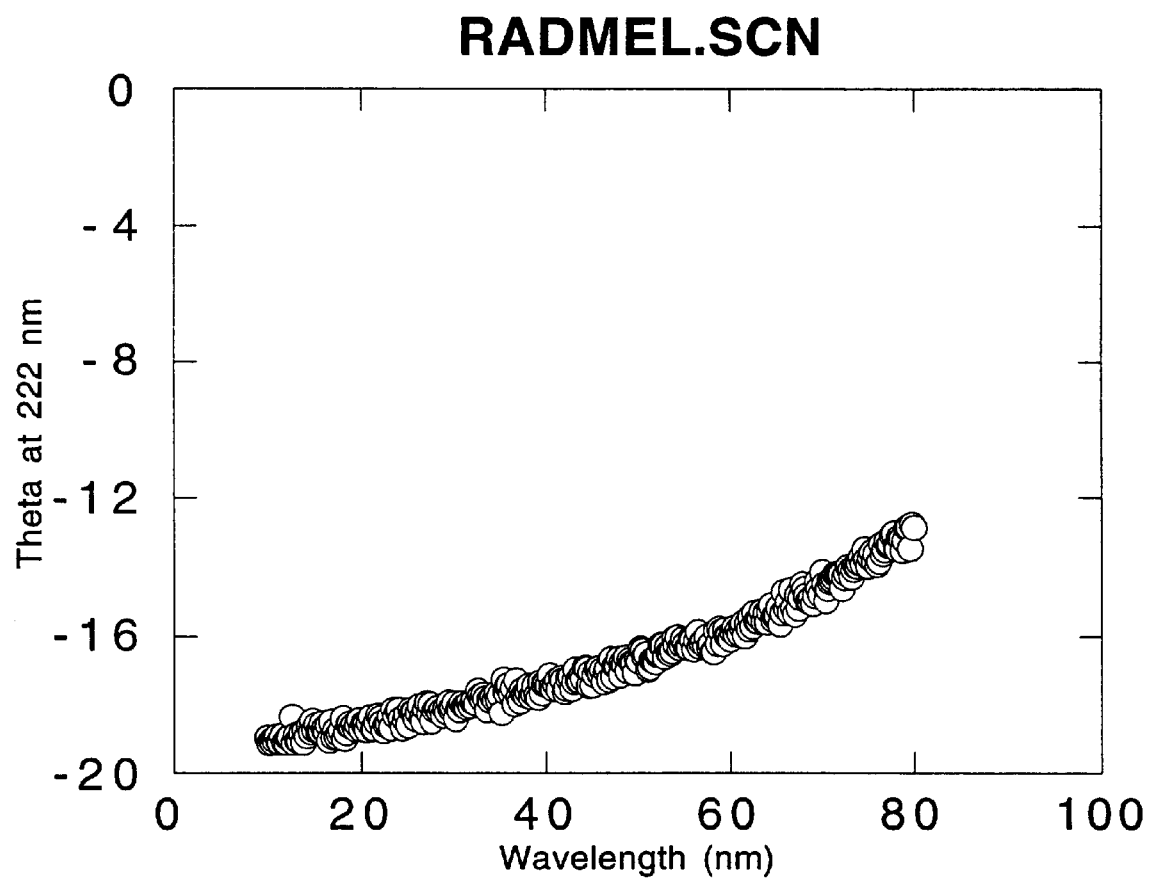
FIG. 18 is a graph showing the melt profile of Rad23 at 222 nm frequency. It is significant to note that there is no temperature dependent unfolding of the protein.

Enhanced Thermostability of RAD23 and Use of the UBL$^{R23}$ Domain to Confer Thermostability On Fusion Proteins Rad23 was purified to homogeneity from bacteria and subjected to structural analysis by circular dichroism (CD-spectra). The analysis was done along with other proteins unrelated to this work. The CD-spectra revealed that Rad23 is a typical globular protein, which is highly soluble and contains substantial α-helical character. See FIG. 17. However, when the thermal stability of the protein was analyzed the data revealed that it did not display the cooperative melting profile typically observed for globular proteins. See FIG. 18. Indeed a melting transition was not detected even when Rad23 was heated to excess of 90° C. Consistent with this result when the protein sample was returned to 23° C. it continued to display CD-spectra consistent with a well-folded globular and soluble protein. In contrast, other proteins that were analyzed at the same time displayed the expected cooperative denaturation at 52° C. indicating that the experimental conditions and the function of the instrument were normal.

The results obtained indicate that the UbL is a cis-acting, temperature stabilizer. As described in the previous examples, UbL$^{R23}$ has been fused to β-galatosidase. Like Rad23, this fusion protein can be heated without loss of secondary structure. Additionally, exposure to high temperatures did not inactivate the enzymatic portion of the fusion protein.

This observation indicates that the UbL has broad applications in the generation of fusion proteins having enhanced thermostability.

REFERENCES

Lam, Y. A., Xu, W., DeMartino, G. N. & Cohen, R. E. *Nature* 385, 737–740 (1997).

Coux, O., Tanaka, K. & Goldberg, A. L. *Annu. Rev. Biochem.* 65, 801–847 (1996).

Masutani, C., et al. *EMBO J.* 13, 1831–1843 (1994). Rubin, D. M., et al. *Nature* 370, 655–657 (1996).

Ausubel, F. M. (1992) *Current Protocols in Molecular Bilogy.* Wiley-Interscience, New York.

Bachmair, A., Finley, D. and Varshavsky, A. 1986. In vivo half-life of a protein is a function of its amino-terminal residue. *Science* 234: 179–186.

Biggins, S., Ivanovska, I. and Rose, R. D. 1996. Yeast ubiquitin-like genes are involved in duplication of the microtubule organizing center. *J. Cell Biol.* 133: 1331–1346.

Boeke, J. D., Lacroute, F. and Fink, G. R. 1984. A positive selection for mutants lacking orotidine-5'-phosphate decarboxylase activity in yeast: 5-fluoro-orotic acid resistance. *Mol. Gen. Genet.* 197: 345–346.

Bootsma, D. and Hoeijmakers, J. H. 1993. DNA repair. Engagement with transcription. *Nature* 363: 220–223. Chen, P., Johnson, P., Sommer, T., Jentsch, S. and Hochstrasser, M. 1993. Multiple ubiquitin-conjugating enzymes participate in the in vivo degradation of the yeast MATα2 repressor. *Cell* 74: 357–369. Finley, D., Bartel, B. and Varshavsky, A. 1989. The tails of ubiquitin precursors are ribosomal proteins whose fusion to ubiquitin facilitates ribosome biogenesis. *Nature* 338: 394–401.

Friedberg, E. C., Walker, G. C. and Siede, W. (1995) *DNA Repair and Mutagenesis.* American Society for Microbiology, Washington, D. C.

Ghislain, M., Udvardy, A. and Mann, C. 1993. S. cerevisiae 26S protease mutants arrest cell division in G2/metaphase. *Nature* 366: 358–361.

Gietz, D., St. John, A., Woods, R. A. and Schiestl, R. H. 1992. Improved method for high efficiency transformation of intact yeast cells. *Nuc. Acids Res.* 20: 1425–1434.

Guthrie, C. and Fink, G. R. (1991) Guide to Yeast *Genetics and Molecular Biology*. Academy Press, New York.

Guzder, S. M., Bailly, V., Sung, P., Prakash, L. and Prakash, S. 1995a. Yeast DNA repair protein RAD23 promotes complex formation between transcription factor TFIIH and DNA damage recognition factor RAD14. *J. Biol. Chem.* 270: 8385–8388.

Guzder, S. N., Habraken, Y., Sung, P., Prakash, L. and Prakash, S. 1995b. Reconstitution of yeast nucleotide excision repair with purified Rad proteins, Replication Protein A, and transcription factor TFIIH. *J. Biol. Chem.* 270: 12973–12976.

Hershko, A. 1991. The ubiquitin pathway for protein degradation. *Trends in Biochem. Sci.* 16: 265–268.

Hicke, L. and Riezman, H. 1996. Ubiquitination of a yeast plasma membrane receptor signals its ligand-stimulated endocytosis. Cell 84: 277–287.

Johnson, E. S., Bartel, B., Seufert, W. and Varshavsky, A. 1992. Ubiquitin as a degradation signal. *EMBO J.* 11: 497–505.

Johnson, E. S., Ma, P. C. M., Ota, I. M. and Varshavsky, A. 1995. A proteolytic pathway that recognizes ubiquitin as a degradation signal. *J. Biol. Chem.* 270: 17442–17456.

Liu, H., Krized, J. and Bretscher, A. 1992. Construction of a GAL1-regulated yeast CDNA expression library and its application to the identification of genes whose overexpression causes lethality in yeast. *Genetics* 132: 665–673.

Madura, K. and Prakash, S. 1990. Transcript levels of the *Saccharomyces cerevisiae* DNA repair gene RAD23 increases in response to UV light and in meiosis but remain constant in the mitotic cell cycle. *Nuc. Acids Res.* 18: 4737–4742.

Madura, K., Prakash, S. and Prakash, L. 1990. Expression of the *Saccharomyces cerevisiae* DNA repair gene RAD6 that encodes a ubiquitin conjugating enzyme, increases in response to DNA damage and in meiosis but remains constant during mitotic cell cycle. *Nuc. Acids Res.* 18: 771–778.

Madura, K. and Varshavsky, A. 1994. Degradation of Gα by the N-end rule pathway. *Science* 265: 1454–1458. Nonet, M., Scafe, C., Sexton, J. and Young, R. 1987. Eukaryotic RNA polymerase conditional mutant that rapidly ceases mRNA synthesis. *Mol. Cell. Biol.* 7: 1602–613.

Ozkaynak, E., Finley, D., Solomon, M. J. and Varshavsky, A. 1990. The yeast ubiquitin genes: A family of natural gene fusions. *EMBO J.* 6: 1429–1439.

Paetkau, D. W., Riese, J. A., MacMorran, W. S., Woods, R. A. and Gietz, R. D. 1994. Interaction of the yeast RAD7 and SIR3 proteins: implications for DNA repair and chromatin structure. *Genes & Dev.* 8: 2035–2045.

Prakash, S., Sung, P. and Prakash, L. 1993. DNA repair genes and proteins of *Saccharomyces cerevisiae*. *Annu. Rev. Genet.* 27: 33–70.

Rothstein, R. 1991. Targeting, disruption, replacement, and allele rescue: integrative DNA transformation in yeast. *Methods Enzymol.* 194: 281–301.

Sancar, A. 1996. DNA Excision Repair. *Annu. Rev. Biochem.* 65: 43–81.

Sanchez, Y., Desany, B. A., Jones, W. J., Liu, Q., Wang, B. and Elledge, S. J. 1996. Regulation of RAD53 by the ATM-like kinases MEC1 and TEL1 in yeast cell cycle check point pathways. *Science* 271: 357–360.

Scheffner, M., Nuber, U. and Huibregtse, J. M. 1995. Protein ubiquitination involving an E1-E2-E3 enzyme ubiquitin thioester cascade. *Nature* 373: 81–81=3.

Schiestl, R. H. and Prakash, S. 1989. Interactions of the RAD7 and RAD23 excision repair genes of *Saccharomyces cerevisiae* with DNA repair genes in different epistasis groups. *Curr. Genet.* 16: 219–223.

Seufert, W. and Jentsch, S. 1990. Ubiquitin-conjugating enzymes UBC4 and UBC5 mediate selective degradation of short-lived and abnormal proteins. *EMBO J.* 9: 543–550.

Sweder, K. S. and Hanawalt, P. C. 1992. Preferential repair of cyclobutane pyrimidine dimers in the transcribed strand of a gene in yeast chromosomes and plasmids is dependent on transcription. *Proc. Natl. Acad. Sci. USA* 89: 10696–10700.

Tokunage, F., Goto, T., Koide, T., Murakami, Y., Hayashi, S.-I., Tamura, T., Tanaka, K. and Ichihara, A. 1994. ATP-and antizyme-dependent endoproteolysis of ornithine decarboxylase to oligopeptides by the 26S proteasome. *J. Biol. Chem.* 269: 17382–17385.

Toniolo et al. 1988. *Proc. Natl. Acad. Sci.* 85:851–855.

van der Spek, P. J., Eker, A., Rademakers, S., Visser, C., Sugasawa, K., Masutani, C., Hanaoka, F., Bootsma, D. and Hoeijmakers, J. H. J. 1996. XPC and human homologs of RAD23: intracellular localization and relationship to other nucleotide excision repair complexes. *Nuc. Acids Res.* 24: 2551–2559.

Varshavsky, A. 1992. The N-end rule. *Cell* 69: 725–735.

Watkins, J. F., Sung, P., Prakash, L. and Prakash, S. 1993. The *Saccharomyces cerevisiae* DNA repair gene RAD23 encodes a nuclear protein containing a ubiquitin-like domain required for biological function. *Mol. Cell. Biol.* 13: 7757–7765.

Wiborg et al. 1985. *EMBO J.* 4:755–759.

Wilcox, D. R. and Prakash, L. 1981. Incision and postincision steps of pyrimidine dimer removal in excision-defective mutants of *Saccharomyces cerevisiae*. *J. Bacteriol.* 148: 618–623.

Ciechanover, A. (1994) Cell 79, 13–21.

Hochstrasser, M. (1996) *Annu. Rev. Genet.* 30, 405–439.

Varshavsky, A. (1997) *Trends Biochem. Sci.* 22, 383–387.

Pickart, C. M. (1997) *FASEB J.* 11, 1055–1066.

Hicke, L. & Riezman, H. (1996) *Cell* 84, 277–287.

Murakami, Y., Matsufuji, S., Kameji, T., Hayashi, S, Igarashi, K., Tamura, T., Tanaka, K. and Ichihara, A. (1992) *Nature* 360, 597–599.

Garrett, K. P., Aso, T., Bradsher, J. N., Foundling, S. I., Lane, W. S., Conaway, R. C. & Conaway, J. W. (1995) *Proc. Natl. Acad. Sci. USA*. 92, 7172–7176.

Shen, Z., Pardington-Purtymun, P. E., Comeaus, J. C., Moyzis, R. K. and Chen, D. J. (1996) *Genomics* 36, 271–279.

Johnson, E. S. a. B., G. (1997) *J. Biol. Chem.* 272, 26799–26802.

Mahajan, R., Delphin, C., Guan, T., Gerace, L. and Melchior, F. (1997) *Cell* 88, 97–107.

Watkins, J. F., Sung, P., Prakash, L. & Prakash, S. (1993) *Mol. Cell. Biol.* 13, 7757–7765.

van der Spek, P. J., Visser, C. C., Hanaoka, F., Smit, B., Hagemeijer, A., Bootsma, D. & Hoeijmakers, J. H. J. (1996) *Genomics* 31, 20–27.

Johnson, E. S., Ma, P. C. M., Ota, I. M. & Varshavsky, A. (1995) *J. Biol. Chem.* 270, 17442–17456.

Bachmair, A., Finley, D. & Varshavsky, A. (1986) *Science* 234, 179–186.

Biggins, S., Ivanovska, I. & Rose, R. D. (1996) *J. Cell Biol.* 133, 1331–1346.

Schauber, C., Potts, W., Kirkpatrick, R. D., Gietz, R. D., Chen, L. and Madura, K. Submitted Guzder, S. N., Sung, P., Prakash, L and Prakash, S. (1996.) *J. Biol. Chem.* 271., 8903–8910.

Madura, K. & Varshavsky, A. (1994) *Science* 265, 1454–1458.

Varshavsky, A. (1992) *Cell* 69, 725–735.

Schauber, C., Chen, L., Tongaonkar, P., Vega, I., Lambertson, D., Potts, W. and Madura, K. (1998) *Nature* (in press).

Kibel, A., Iliopoulos, O., DeCaprio, J. & Kaelin, W. (1995) *Science* 269, 1444–1446.

Coux, O., Tanaka, K. & Goldberg, A. L. (1996) *Annu. Rev. Biochem.* 65, 801–847.

Chau, V., Tobias, J. W., Bachmair, A., Marriott, D., Ecker, D., Gonda, D. K. & Varshavsky, A. (1989) *Science* 243, 1576–1583.

Ghislain, M., Udvardy, A. & Mann, C. (1993) *Nature* 366, 358–361.

DeMarini, D. J., Papa, F. R., Swaminathan, S., Ursic, D., Rasmussen, T. P., Culbertson, M. R. & Hochstrasser, M. (1995) *Mol. Cell. Biol.* 15.

Merrick, W. C. (1979) *Meth. Enzymol.* 60, 108–123.

Heinemeyer, W., Kleinschmidt, J. A., Saidowsky, J., Escher, C. & Wolf, D. H. (1991) *EMBO J.* 10, 555–562.

Masutani, C., Sugasawa, K., Yanagisawa, J., Sonoyama, T., Ui, M., Enomoto, T., Takio, K., Tanaka, K., van der Spek, P. J., Bootsma, P. J., Hoeijmakers, J. H. J. & Hanaoka, F. (1994) *EMBO J.* 13, 1831–1843.

van Nocker, S., Sadis, S., Rubin, D. M., Glickman, M., Fu, H., Coux, O., Wefes, I., Finley, D. & Vierstra, R. D. (1996) *Mol. Cell. Biol.* 16, 6020–6028.

Murakami, Y., Tanaka, D., Matsufuji, Y. and Hayashi, S. (1992) *Biochem. J.* 283, 661–664.

Guzder, S. N., Habraken, Y., Sung, P., Prakash, L. & Prakash, S. (1995) *J. Biol. Chem.* 270, 12973–12976.

Wang, Z., Wei, S., Reed, S. H., Wu, X., Svejstrup, J. Q., Feaver, W. J., Kornberg, R. D. and Friedberg, E. C. (1997) *Mol. Cell. Biol.* 17, 635–643.

Miller, R. D., Prakash, L. & Prakash, S. (1982) *Mol. Gen. Genet.* 188, 235–239.

Gaczynska, M., Rock, K. L. & Goldberg, A. L. (1993) *Nature* 365, 264–267.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for rapid and efficient purification of proteasomes from cells comprising:
    a) providing one or more polypeptides comprising an amino acid sequence homologous to ubiquitin, selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12;
    b) immobilizing the polypeptide to a solid support;
    c) exposing the immobilized polypeptide to a cell lysate;
    d) washing non-specifically bound proteins from the immobilized polypeptide; and
    e) eluting said proteasomes from said solid support, thereby purifying the proteasome from the cell lysate.

2. A method as claimed in claim 1, wherein the sequence homologous to ubiquitin and the cell lysate are isolated from the same species.

3. A kit for the rapid purification of proteasomes from a cell lysate, said kit containing: one or more polypeptides comprising an amino acid sequence selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12 affixed to a solid support, one or more containers, a wash solution and an elution buffer.

4. A kit as claimed in claim 3, further comprising a solution useful in performing a purification method of the invention, selected from the group consisting of saline, buffer, diluent, and frozen cell extract.

* * * * *

SEQUENCE LISTING

```
<160> NUMBER OF SEQ ID NOS: 17

<210> SEQ ID NO 1
<211> LENGTH: 76
<212> TYPE: PRT
<213> ORGANISM: Artificial Sequence
<220> FEATURE:
<223> OTHER INFORMATION: Synthetic Sequence

<400> SEQUENCE: 1

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 2
<211> LENGTH: 77
<212> TYPE: PRT
<213> ORGANISM: Artificial Sequence
<220> FEATURE:
<223> OTHER INFORMATION: Synthetic Sequence

<400> SEQUENCE: 2

Met Ser Leu Asn Ile His Ile Lys Ser Gly Gln Asp Lys Trp Glu Val
1               5                   10                  15

Asn Val Ala Pro Glu Ser Thr Leu Val Gln Phe Lys Glu Ala Ile Asn
            20                  25                  30

Lys Ala Asn Gly Ile Pro Val Ala Asn Gln Arg Leu Ile Tyr Ser Gly
        35                  40                  45
```

-continued

Lys Ile Leu Lys Asp Asp Gln Thr Val Glu Ser Tyr His Ile Gln Asp
            50                  55                  60

Gly His Ser Val His Leu Val Lys Ser Gln Pro Lys Pro
65                  70                  75

<210> SEQ ID NO 3
<211> LENGTH: 77
<212> TYPE: PRT
<213> ORGANISM: Artificial Sequence
<220> FEATURE:
<223> OTHER INFORMATION: Synthetic Sequence

<400> SEQUENCE: 3

Met Val Ser Leu Thr Phe Lys Asn Phe Lys Glu Lys Val Pro Leu
1               5                   10                  15

Asp Leu Glu Pro Ser Asn Thr Ile Leu Glu Thr Lys Thr Lys Leu Ala
            20                  25                  30

Gln Ser Ile Ser Cys Glu Glu Ser Gln Ile Lys Leu Ile Tyr Ser Gly
            35                  40                  45

Lys Val Leu Gln Asp Ser Leu Thr Val Ser Glu Cys Gly Leu Lys Asp
            50                  55                  60

Gly Asp Gln Val Val Phe Met Val Ser Gln Lys Lys Ser
65                  70                  75

<210> SEQ ID NO 4
<211> LENGTH: 79
<212> TYPE: PRT
<213> ORGANISM: Artificial Sequence
<220> FEATURE:
<223> OTHER INFORMATION: Synthetic Sequence

<400> SEQUENCE: 4

Met Gln Val Thr Leu Lys Thr Leu Gln Gln Gln Thr Phe Lys Ile Asp
1               5                   10                  15

Ile Asp Pro Glu Glu Thr Val Lys Ala Leu Lys Glu Lys Ile Glu Ser
            20                  25                  30

Glu Lys Gly Lys Asp Ala Phe Pro Val Ala Gly Gln Lys Leu Ile Tyr
            35                  40                  45

Ala Gly Lys Ile Leu Asn Asp Asp Thr Ala Leu Lys Glu Tyr Lys Ile
            50                  55                  60

Asp Glu Lys Asn Phe Val Val Met Val Thr Lys Pro Lys Ala
65                  70                  75

<210> SEQ ID NO 5
<211> LENGTH: 81
<212> TYPE: PRT
<213> ORGANISM: Artificial Sequence
<220> FEATURE:
<223> OTHER INFORMATION: Synthetic Sequence

<400> SEQUENCE: 5

Met Ala Val Thr Ile Thr Leu Lys Thr Leu Gln Gln Gln Thr Phe Lys
1               5                   10                  15

Ile Arg Met Glu Pro Asp Glu Thr Val Lys Val Leu Lys Glu Lys Ile
            20                  25                  30

Glu Ala Glu Lys Gly Arg Asp Ala Phe Pro Val Ala Gly Gln Lys Leu
            35                  40                  45

Ile Tyr Ala Gly Lys Ile Leu Ser Asp Asp Val Pro Ile Arg Asp Tyr
            50                  55                  60

```
Arg Ile Asp Glu Lys Asn Phe Val Val Met Val Thr Lys Thr Lys
 65                  70                  75                  80

Ala
```

<210> SEQ ID NO 6
<211> LENGTH: 83
<212> TYPE: PRT
<213> ORGANISM: Artificial Sequence
<220> FEATURE:
<223> OTHER INFORMATION: Synthetic Sequence

<400> SEQUENCE: 6

```
Ala Val His Leu Thr Leu Lys Lys Ile Gln Ala Pro Lys Phe Ser Ile
 1               5                  10                  15

Glu His Asp Phe Ser Pro Ser Asp Thr Ile Leu Gln Ile Lys Gln His
                20                  25                  30

Leu Ile Ser Glu Glu Lys Ala Ser His Ile Ser Glu Ile Lys Leu Leu
            35                  40                  45

Leu Lys Gly Lys Val Leu His Asp Asn Leu Phe Leu Ser Asp Leu Lys
 50                  55                  60

Val Thr Pro Ala Asn Ser Thr Ile Thr Val Met Ile Lys Pro Asn Pro
 65                  70                  75                  80

Thr Ile Ser
```

<210> SEQ ID NO 7
<211> LENGTH: 76
<212> TYPE: PRT
<213> ORGANISM: Artificial Sequence
<220> FEATURE:
<223> OTHER INFORMATION: Synthetic Sequence

<400> SEQUENCE: 7

```
Met Ile Val Lys Val Lys Thr Leu Thr Gly Lys Glu Ile Ser Val Glu
 1               5                  10                  15

Leu Lys Glu Ser Asp Leu Val Tyr His Ile Lys Glu Leu Leu Glu Glu
                20                  25                  30

Lys Glu Gly Ile Pro Pro Ser Gln Gln Arg Leu Ile Phe Gln Gly Lys
            35                  40                  45

His Ser Asp Asp Lys Leu Thr Val Thr Asp Ala His Leu Val Glu Gly
 50                  55                  60

Met Gln Leu Lys Leu Val Leu Thr Leu Arg Gly Gly
 65                  70                  75
```

<210> SEQ ID NO 8
<211> LENGTH: 83
<212> TYPE: PRT
<213> ORGANISM: Artificial Sequence
<220> FEATURE:
<223> OTHER INFORMATION: Synthetic Sequence

<400> SEQUENCE: 8

```
Glu Glu Ile Ala Ala Phe Arg Ile Phe Arg Lys Ser Thr Ser Asn
 1               5                  10                  15

Leu Lys Ser Ser His Thr Thr Ser Asn Leu Val Lys Lys Thr Met Phe
                20                  25                  30

Lys Arg Asp Leu Leu Lys Gln Asp Pro Lys Arg Lys Leu Gln Leu Gln
            35                  40                  45

Gln Arg Phe Ala Ser Pro Thr Asp Arg Leu Val Ser Pro Cys Ser Leu
 50                  55                  60
```

```
Lys Leu Asn Glu His Lys Val Lys Met Phe Gly Lys Lys Lys Val
 65                  70                  75                  80

Asn Pro Met
```

<210> SEQ ID NO 9
<211> LENGTH: 101
<212> TYPE: PRT
<213> ORGANISM: Artificial Sequence
<220> FEATURE:
<223> OTHER INFORMATION: Synthetic Sequence

<400> SEQUENCE: 9

```
Met Ser Asp Gln Glu Ala Lys Pro Ser Thr Glu Asp Leu Gly Asp Lys
  1               5                  10                  15

Lys Glu Gly Glu Tyr Ile Lys Leu Lys Val Ile Gly Gln Asp Ser Ser
                 20                  25                  30

Glu Ile His Phe Lys Val Lys Met Thr Thr His Leu Lys Lys Leu Lys
             35                  40                  45

Glu Ser Tyr Cys Gln Arg Gln Gly Val Pro Met Asn Ser Leu Arg Phe
         50                  55                  60

Leu Phe Glu Gly Gln Arg Ile Ala Asp Asn His Thr Pro Lys Glu Leu
 65                  70                  75                  80

Gly Met Glu Glu Glu Asp Val Ile Glu Val Tyr Gln Glu Gln Thr Gly
                 85                  90                  95

Gly His Ser Thr Val
                100
```

<210> SEQ ID NO 10
<211> LENGTH: 95
<212> TYPE: PRT
<213> ORGANISM: Artificial Sequence
<220> FEATURE:
<223> OTHER INFORMATION: Synthetic Sequence

<400> SEQUENCE: 10

```
Met Ala Asp Glu Lys Pro Lys Glu Gly Val Lys Thr Glu Asn Asn Asp
  1               5                  10                  15

His Ile Asn Leu Lys Val Ala Gly Gln Asp Gly Ser Val Val Gln Phe
                 20                  25                  30

Lys Ile Lys Arg His Thr Pro Leu Ser Lys Leu Met Lys Ala Tyr Cys
             35                  40                  45

Glu Arg Gln Gly Leu Ser Met Arg Gln Ile Arg Phe Arg Phe Asp Gly
         50                  55                  60

Gln Pro Ile Asn Glu Thr Asp Thr Pro Ala Gln Leu Glu Met Glu Asp
 65                  70                  75                  80

Glu Asp Thr Ile Asp Val Phe Gln Gln Gln Thr Gly Gly Val Tyr
                 85                  90                  95
```

<210> SEQ ID NO 11
<211> LENGTH: 95
<212> TYPE: PRT
<213> ORGANISM: Artificial Sequence
<220> FEATURE:
<223> OTHER INFORMATION: Synthetic Sequence

<400> SEQUENCE: 11

```
Met Ser Glu Glu Lys Pro Lys Glu Gly Val Lys Thr Glu Asn Asp His
  1               5                  10                  15

Ile Asn Leu Lys Val Ala Gly Gln Asp Gly Ser Val Val Gln Phe Lys
                 20                  25                  30
```

Ile Lys Arg His Thr Ser Leu Ser Lys Leu Met Lys Ala Tyr Cys Glu
                35                  40                  45

Arg Gln Gly Leu Ser Met Arg Gln Ile Arg Phe Arg Phe Asp Gly Gln
            50                  55                  60

Pro Ile Asn Glu Thr Asp Thr Pro Ala Gln Leu Arg Met Glu Asp Glu
65                  70                  75                  80

Asp Thr Ile Asp Val Phe Gln Gln Gln Thr Gly Val Pro Glu
                85                  90                  95

<210> SEQ ID NO 12
<211> LENGTH: 100
<212> TYPE: PRT
<213> ORGANISM: Artificial Sequence
<220> FEATURE:
<223> OTHER INFORMATION: Synthetic Sequence

<400> SEQUENCE: 12

Met Ser Asp Ser Glu Val Asn Gln Glu Ala Lys Pro Glu Val Lys Pro
1               5                   10                  15

Glu Val Lys Pro Glu Thr His Ile Asn Leu Lys Val Ser Asp Gly Ser
            20                  25                  30

Ser Glu Ile Phe Phe Lys Ile Lys Lys Thr Thr Pro Leu Arg Arg Leu
                35                  40                  45

Met Glu Ala Phe Ala Lys Arg Gln Gly Lys Glu Met Asp Ser Leu Arg
            50                  55                  60

Phe Leu Tyr Asp Gly Ile Arg Ile Gln Ala Asp Gln Thr Pro Glu Asp
65                  70                  75                  80

Leu Asp Met Glu Asp Asn Asp Ile Ile Glu Ala His Arg Glu Gln Ile
                85                  90                  95

Gly Gly Ala Thr
            100

<210> SEQ ID NO 13
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 13
gcgaattcat ggttagctta acc                                           23

<210> SEQ ID NO 14
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 14
gcggtacccg tcggcatgat cgctg                                         25

<210> SEQ ID NO 15
<211> LENGTH: 32
<212> TYPE: DNA
<213> ORGANISM: Artificial Sequence
<220> FEATURE:
<223> OTHER INFORMATION: Synthetic Sequence

<400> SEQUENCE: 15
gcgaattcat gacgaagacc aaactaacag aa                                 32

-continued

```
<210> SEQ ID NO 16
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 16
gaagataccc caccaaac                                              18

<210> SEQ ID NO 17
<211> LENGTH: 9
<212> TYPE: PRT
<213> ORGANISM: Influenza virus

<400> SEQUENCE: 17

Tyr Pro Tyr Asp Val Pro Asp Tyr Ala
 1               5
```